(12) United States Patent
Pandolfino

(10) Patent No.: US 9,814,258 B2
(45) Date of Patent: Nov. 14, 2017

(54) REDUCED-EXPOSURE TOBACCO PRODUCTS

(75) Inventor: Joseph Pandolfino, Clarence, NY (US)

(73) Assignee: 22nd Century Limited, LLC, Clarence, NY (US)

( * ) Notice: Subject to any disclaimer, the term of this patent is extended or adjusted under 35 U.S.C. 154(b) by 1685 days.

(21) Appl. No.: 10/568,290

(22) PCT Filed: Aug. 18, 2004

(86) PCT No.: PCT/US2004/026815
§ 371 (c)(1),
(2), (4) Date: Feb. 16, 2006

(87) PCT Pub. No.: WO2005/018307
PCT Pub. Date: Mar. 3, 2005

(65) Prior Publication Data
US 2007/0034220 A1    Feb. 15, 2007

Related U.S. Application Data

(60) Provisional application No. 60/496,290, filed on Aug. 19, 2003.

(51) Int. Cl.
*A24B 15/00* (2006.01)
*A24B 15/10* (2006.01)
*C12N 15/82* (2006.01)

(52) U.S. Cl.
CPC .............. *A24B 15/10* (2013.01); *A24B 15/00* (2013.01); *C12N 15/8243* (2013.01)

(58) Field of Classification Search
None
See application file for complete search history.

(56) References Cited

U.S. PATENT DOCUMENTS 3,258,015 A    6/1966 Ellis et al.
3,356,094 A    12/1967 Ellis et al.
(Continued)

FOREIGN PATENT DOCUMENTS

CN    1259321    7/2000
EP    0 486 214 A2    5/1992
(Continued)

OTHER PUBLICATIONS

Baskevitch, N.; Ferrer, G., "Modification of Nicotine to Tar Ratio Through the Use of Reconstituted Tobacco", 1982, CORESTA.*
(Continued)

*Primary Examiner* — Michael J Felton
(74) *Attorney, Agent, or Firm* — Foley & Lardner LLP

(57) ABSTRACT

The present invention provides methodologies, including the utilization of genetically modified (GM) tobaccos, for the development and production of consumer acceptable PREPs encompassing the following: 1) production of low tar-to-nicotine ratio cigarettes, which allow smokers to obtain satisfying amounts of nicotine more efficiently than conventional cigarettes while reducing whole smoke deliveries; thereby reducing smoker "compensation" that exists with conventional low-yield cigarettes; 2) reduction of harmful tobacco-specific nitrosamines in tobacco products by genetic means and by extracting nicotine from tobacco and combining such with genetically modified reduced-nicotine tobacco; 3) production of improved expanded tobacco which utilizes genetically modified increased-nicotine tobacco; and 4) production of reconstituted tobacco which includes any combinations of the following: genetically modified increased-nicotine tobacco, genetically modified reduced-nicotine tobacco, tobacco leaf fractions, and freshly harvested freeze-dried tobacco.

3 Claims, 6 Drawing Sheets

Comparison between Vector Burley 21-41 and Burley 21 LA

| | Vector Burley 21-41 | TREATMENT Promoter Control | Wild-type |
|---|---|---|---|
| Days from transplant to flowering (days) | 57.1 ± 3.6* | 56.7 ± 3.4* | 57.6 ± 3.4* |
| Height at flowering (cm) | 118.6 ± 20.1* | 112.1 ± 21.4* | 110.8 ± 19.5* |
| Yield (kg/ha) | 890.3 ± 70.7* | 780 ± 68.5* | 809.2 ± 71.2* |
| % Nicotine (X $10^2$) | 1.44 ± 0.66** | 19.12 ± 8.99* | 21.54 ± 9.34* |
| % Nor-Nicotine (X $10^2$) | 0.4 ± 0.1** | 1.56 ± 0.22* | 1.27 ± 0.52* |
| % Total Alkaloids | 0.23 ± 0.07** | 2.07 ± 0.93* | 2.31 ± 0.94* |
| % Total Nitrogen | 2.52 ± 0.78* | 2.96 ± 0.42* | 2.64 ± 0.91* |
| % Reducing Sugars | 10.29 ± 0.89** | 5.87 ± 2.04* | 5.51 ± 2.40* |

Data from 2000 field trial at Central Crops Research Station, Clayton, NC. Chemical analysis was carried out on topped plants. 15 replicates/10 plants per replicate.
Data were analyzed using the F-test.

* = No significant difference, ** = Significant at the 1% level.

(56) References Cited

U.S. PATENT DOCUMENTS

| | | |
|---|---|---|
| 3,499,454 A | 3/1970 | Hind |
| 3,861,400 A * | 1/1975 | Perkins et al. ............... 131/335 |
| 3,878,850 A * | 4/1975 | Gibson et al. ............... 131/275 |
| 3,957,060 A * | 5/1976 | Newton et al. ............... 131/276 |
| 3,991,772 A | 11/1976 | Smith, Jr. |
| 4,182,349 A | 1/1980 | Selke |
| 4,289,147 A | 9/1981 | Wildman et al. |
| 4,326,358 A | 4/1982 | Lawrence, Jr. et al. |
| 4,336,814 A | 6/1982 | Sykes et al. |
| 4,340,073 A | 7/1982 | de la Burde et al. |
| 4,347,324 A | 8/1982 | Wildman et al. |
| 4,381,624 A | 5/1983 | Lawrence, Jr. et al. |
| 4,531,529 A | 7/1985 | White et al. |
| 4,830,028 A | 5/1989 | Lawson et al. |
| 4,836,224 A | 6/1989 | Lawson et al. |
| 4,962,774 A | 10/1990 | Thomasson et al. |
| 4,987,071 A | 1/1991 | Cech et al. |
| 5,031,646 A | 7/1991 | Lippiello et al. |
| 5,260,205 A | 11/1993 | Nakatani et al. |
| 5,272,065 A | 12/1993 | Inouye et al. |
| 5,369,023 A | 11/1994 | Nakatani et al. |
| 5,580,967 A | 12/1996 | Joyce |
| 5,583,032 A | 12/1996 | Torrence et al. |
| 5,589,367 A | 12/1996 | Donson et al. |
| 5,591,601 A | 1/1997 | Wagner et al. |
| 5,622,854 A | 4/1997 | Draper |
| 5,668,295 A | 9/1997 | Wahab et al. |
| 5,773,689 A | 6/1998 | Thompson et al. |
| 5,773,695 A | 6/1998 | Thompson et al. |
| 5,803,081 A | 9/1998 | O'Donnell, Jr. et al. |
| 5,845,647 A | 12/1998 | O'Donnell, Jr. et al. |
| 6,037,525 A | 3/2000 | Thompson et al. |
| 6,100,448 A | 8/2000 | Thompson et al. |
| 6,135,121 A | 10/2000 | Williams |
| 6,202,649 B1 | 3/2001 | Williams |
| 6,311,695 B1 | 11/2001 | Williams |
| 6,338,348 B1 | 1/2002 | Williams |
| 6,350,479 B1 | 2/2002 | Williams et al. |
| 6,423,520 B1 | 7/2002 | Conkling et al. |
| 6,425,401 B1 | 7/2002 | Williams |
| 6,534,527 B2 | 3/2003 | Wolfson et al. |
| RE38,123 E | 5/2003 | Williams |
| 6,569,470 B2 | 5/2003 | Williams et al. |
| 6,586,661 B1 | 7/2003 | Hunt et al. |
| 6,761,175 B2 | 7/2004 | Nakanishi et al. |
| 2002/0174874 A1 | 11/2002 | Williams |
| 2002/0197688 A1 | 12/2002 | Pandolfino |
| 2003/0018997 A1 | 1/2003 | Conkling et al. |
| 2004/0144397 A1 | 7/2004 | Conkling |

FOREIGN PATENT DOCUMENTS

| | | |
|---|---|---|
| WO | WO 98/56923 | 12/1998 |
| WO | WO 00/67558 | 11/2000 |
| WO | WO 02/100199 A2 | 12/2002 |
| WO | WO 03/013226 A2 | 2/2003 |

OTHER PUBLICATIONS

Sato, F., et al., "Metabolic engineering of plant alkaloid biosynthesis", Jan. 2, 2001, PNAS, col. 98, pp. 367-372.*

Michael A. H. Russell et al., "Public Health and Levels of Nicotine: Should Nicotine Levels in Cigarettes Be Minimized or Maximized?" Nicotine and Public Health, 2000, XP002394926.

Action on Smoking and Health—Mar. 2006 Factsheet No. 18, The UK tobacco industry.

"Clearing the Smoke—Assessing the Science Base for Tobacco Harm Reduction", (IOM Report), Institute of Medicine, Washington DC: National Academy Press, 2001.

Dietrich Hoffmann et al., "The Changing Cigarette: Chemical Studies and Bioassays", Chapter 5, Smoking and Tobacco Control Monograph No. 13, NIH Pub. No. 02-5074, Oct. 2001, pp. 159-192.

Gio Batta Gori, "Virtually Safe Cigarettes Reviving an Opportunity Once Tragically Rejected", Health Policy Center, Bethesda, MD., 2000.

J.C. Leffingwell, Chapter 8, Leaf Chemistry, Tobacco: Production, Chemistry and Technology, pp. 275-276, 1999.

Lynn T. Kozlowski et al., "Cigarette Design", Chapter 2, Nov. 19, 2001, pp. 13-38.

C.W. Bacon et al., "Chemical Changes in Tobacco during Flue-Curing", Industrial and Engineering Chemistry, Feb. 1952, pp. 292-296.

Subparagraph (A), Federal Cigarette Labeling and Advertising Act, 89th Congress 1st Session, Report No. 449, pp. 1-21.

Neil D. Weinstein, "Public Understanding of Risk and Reasons for Smoking Low-Yield Product", Chapter 6, Nov. 19, 2001, pp. 193-198.

Gio B. Gori, "Consumer Perception of Cigarette Yields: Is the Message Relevant?", Regulatory Toxicology and Pharmacology, 12, pp. 64-68, (1990).

J.L. White et al., "Effect of pyrolysis temperature on the mutagenicity of tobacco smoke condensate", Food and Chemical Toxicology 39, (2001), pp. 499-505.

Neil L. Benowitz, "Compensatory Smoking of Low Yield Cigarettes", Smoking and Tobacco Control Monograph No. 13, Chapter 3, Nov. 19, 2001, pp. 39-63.

E.A. Wernsman et al., "Tobacco", Principles of Cultivar Development, vol. 2, Chapter 17, Crop Species Ed. W.R. Fehr, Macmillan, New York 1987, pp. 669-699.

Gio Batta Gori, "Less-Hazardous Cigarettes, the Case for Hastening Their Regulation and Promotion", Tobacco Reporter, Jun. 2004, pp. 30-34.

Michael A.H. Russell, "The Case for Medium-Nicotine Low-Tar, Low-Carbon Monoxide Cigarettes", Banbury Report a Safe Cigarette, 1980, pp. 297-310.

"Shameful science: four decades of the German tobacco industry's hidden research on smoking and health", Tobacco Control 2000: 9, pp. 242-247.

Yupynn Chintapakorn et al., "Antisense-mediated down-regulation of putrescine N-methyltransferase activity in transgenic *Nicotiana tabacum* L. can lead to elevated levels of anatabine at the expense of nicotine", Plant Molecular Biology 53: 87-105, 2003.

D.M. Peele et al., "Formation of tobacco specific nitrosamines in flu-cured tobacco", CORESTA 1999, AGRO-PHYTO Proceedings Suzhou, China, 1999.

Gerald P. Morie, "Fraction of Protonated and Unprotonated Nicotine in Tobacco Smoke At Various pH Values", Tobacco Science, 167, 1972.

B.L. Miki et al., "Procedures for Introducing Foreign DNA into Plants", Methods in Plant Biology & Biotechnology, 1993, pp. 67-88.

"Status update of sugar/nicotine balance technology assessment", 1992, RJ Reynolds documents Bates 512842551/2.

Low Delivery Cigarettes and Increased Nicotine/Tar Ratios, A Replication (R2-3537), Phillip Morris U.S. Research Center, 1975, Bates 2056140416.

Siqing Song et al., "Supercritical Fluid Extraction and Gas Chromatography/Mass Spectrometry for the Analysis of Tobacco-Specific Nitrosamines in Cigarettes", Anal. Chem, 1999, vol. 71, No. 7, pp. 1303-1308.

Molecular Cloning, A Laboratory Manual Second Edition, Cold Spring Harbor Laboratory Press, 1989.

Paul D. Legg et al., "Inheritance of Per Cent Total Alkaloids in *Nicotiana tabacum* L. II. Genetic Effects of Two Loci in Burley 21 X LA Burley 21 Populations", Can. J. Genet. Cytol. 13: 287-291, 1971.

William L. Clapp et al., "Reduction in Ames Salmonella mutagenicity of mainstream cigarette smoke condensate by tobacco protein removal", Mutation Research 446 (1999) pp. 167-174.

Edward Leete, "Biosynthesis and Metabolism of the Tobacco Alkaloids—Chapter 3", Alkaloids Chemical and Biological Perspectives, vol. 1, Jan. 25, 1988, pp. 85-152.

H.C. Pillsbury et al., "Tobacco—Tar and Nicotine in Cigarette Smoke", Journal of the Association of Official Analytical Chemists, vol. 52, No. 3, May 1969, pp. 458-462.

(56) References Cited

OTHER PUBLICATIONS

Jed E. Rose, "The Role of Upper Airway Stimulation in Smoking", Nicotine Replacement: A Critical Evaluation, pp. 95-106, 1988.
Dietrich Hoffman et al., "Origin in Tobacco Smoke of N'-Nitrosonornicotine, a Tobacco-Specific Carcinogen: Brief Communication [1,2,3]", J. Natl Cancer Inst, vol. 58, No. 6, Jun. 1977, pp. 1841-1844.
Gio Batta Gori, "Virtually Safe Cigarettes Reviving an Opportunity Once Tragically Rejected", IOS Press, The Netherlands, 2000.
M A H Russell, "Low-tar medium-nicotine cigarettes: a new approach to safer smoking", British Medical Journal, Jun. 12, 1976, pp. 1430-1433.
Brown and Williamson Tobacco Company research in the Journal of the American Medical Association, vol. 274, No. 3, pp. 228, 1995.
T. Matsumoto et al., "Mutagenicities of the Pyrolyzates of Peptides and Proteins", Mutation Research, 56 (1978) pp. 281-288.
Directive 2001/37/EC of the European Parliament and Council of Jun. 5, 2001.
Office Action issued in related Australia Patent Application No. AR 045466 A1, dated Jul. 28, 2014.

\* cited by examiner

FIGURE 2

Comparison of TNR's of Popular Brands*

| | Tar | Nic. | TNR | |
|---|---|---|---|---|
| Marlboro Kings Filter Soft Pack | 15 | 1.1 | 13.64 | |
| Marlboro Medium Kings Filter Soft Pack | 11 | 0.8 | 13.75 | |
| Marlboro Lights Kings Filter Soft Pack | 11 | 0.8 | 13.75 | |
| Marlboro Ultra Lights Kings Filter Box | 6 | 0.5 | 13.75 | |
| Marlboro 100's Filter Box Red | 15 | 1.1 | 13.75 | |
| Basic Full Flavor Kings Filter Box | 16 | 1 | 16.00 | |
| Basic Lights Kings Filter Box | 10 | 0.7 | 14.29 | |
| Basic Ultra Lights Kings Filter Soft Pack | 6 | 0 5 | 12.00 | |
| Basic Full Flavor 100's Filter Soft Pack | 16 | 1 | 16.00 | |
| Virginia Slims Full Flavor 100's Filter Box | 15 | 1.1 | 13 64 | |
| Virginia Slims Lights 120's Filter Menthol Box | 14 | 1.1 | 12.73 | |
| GPC Full Flavor King | 15 | 0.8 | 18.75 | (Highest) |
| GPC Lights King Box | 9 | 0.6 | 15.00 | |
| GPC Ultra Lights King | 5 | 0.4 | 12.50 | |
| GPC Menthol Full Flavor 100 | 13 | 0.8 | 16.25 | |
| Lucky Strike Non-Filter | 23 | 1.5 | 15.33 | |
| Lucky Strike Filter King Box | 15 | 1.1 | 13.64 | |
| Lucky Strike Lights King Box | 9 | 0.8 | 11.25 | (Lowest) |

* These brands represent about 50 % of U S market

FIGURE 4

Comparison between Vector Burley 21-41 and Burley 21 LA

|  | TREATMENT | | |
|---|---|---|---|
|  | Vector Burley 21-41 | Promoter Control | Wild-type |
| Days from transplant to flowering (days) | 57.1 ± 3.6* | 56.7 ± 3.4* | 57.6 ± 3.4* |
| Height at flowering (cm) | 118.6 ± 20.1* | 112.1 ± 21.4* | 110.8 ± 19.5* |
| Yield (kg/ha) | 890.3 ± 70.7* | 780 ± 68.5* | 809.2 ± 71.2* |
| % Nicotine (X $10^2$) | 1.44 ± 0.66** | 19.12 ± 8.99* | 21.54 ± 9.34* |
| % Nor-Nicotine (X $10^2$) | 0.4 ± 0.1** | 1.56 ± 0.22* | 1.27 ± 0.52* |
| % Total Alkaloids | 0.23 ± 0.07** | 2.07 ± 0.93* | 2.31 ± 0.94* |
| % Total Nitrogen | 2.52 ± 0.78* | 2.96 ± 0.42* | 2.64 ± 0.91* |
| % Reducing Sugars | 10.29 ± 0.89** | 5.87 ± 2.04* | 5.51 ± 2.40* |

Data from 2000 field trial at Central Crops Research Station, Clayton, NC. Chemical analysis was carried out on topped plants. 15 replicates/10 plants per replicate.
Data were analyzed using the F-test.

* = No significant difference, ** = Significant at the 1% level.

REDUCED-EXPOSURE TOBACCO PRODUCTS

BENEFIT OF PROVISIONAL APPLICATION

This patent application claims the benefit of U.S. Provisional Application No. 60/496,290, filed Aug. 19, 2003; the entire content of which is hereby incorporated by reference.

TECHNICAL FIELD

The present invention relates to the field of reduced-exposure tobacco products, including but not limited to cigarettes which contain genetically modified tobacco and methods of producing such cigarettes.

BACKGROUND

Tobacco use is considered to be a preventable cause of major illness and death in the United States (U.S. Department of Health and Human Services (U.S. DHHS), January 2000, *Healthy People* 2010). During the past several decades, the public health community has repeatedly highlighted the health consequences of smoking cigarettes. Cardiovascular diseases, respiratory diseases and cancers that are attributable to smoking are extensive and growing, as evidenced by the most recent Surgeon General Report (The Health Consequences of Smoking, Surgeon General's Report, 2004). The Center for Disease Control has estimated that more than 440,000 premature deaths per year in the U.S. are attributable to cigarette smoking (Center for Disease Control, Targeting Tobacco Use, 2004).

While smoking rates in the developed world have leveled off over the last thirty years, and have even decreased in some countries, smoking rates and cigarette consumption rates in the developing world have increased during this same time period and will likely continue to do so for the foreseeable future. Current projections show that the number of smokers worldwide will increase from the present 1.3 billion to more than 1.7 billion in 2025 (due in part to an increase in global population) if the global prevalence of tobacco remains unchanged (World Health Organization, 2004).

Total cigarette consumption worldwide continues to increase. In terms of volume, total world consumption of cigarettes increased by 4 percent between 1995 and 1999, from 4.763 trillion cigarettes to 4.953 trillion cigarettes. The manufactured tobacco-products market is dominated by cigarettes, which account for 96 percent of global market value (The World Market for Tobacco Products, published by Euromonitor International, 2000 Edition, p. 2). In 2002, the worldwide market grew to 5.322 trillion cigarettes (Action on Smoking and Health, Factsheet No:18; January, 2004).

Considering the magnitude and growth rate of these numbers, it is clear that people will be smoking cigarettes for a long time to come. It is predicted that cigarette smoking could cause up to one billion premature deaths worldwide by the end of the $21^{st}$ Century. Present statistics demonstrate that there is about one lung cancer death for every 3 million cigarettes consumed (Nature Cancer Reviews, October 2001).

The ideal solution to this health care dilemma is for all cigarette smokers to quit. However, such a solution appears unrealistic. Prohibitionist anti-tobacco policies from the anti-tobacco lobby have been unsuccessful for the most part given the increasing worldwide consumption of tobacco products. These policies in the Western world, where they are most prevalent, have hardly reduced smoking rates over the last twenty years. A significant percentage of cigarette smokers have no desire to quit smoking. Even though tens of millions of people in the U.S. alone have quit smoking, many before the advent of the many forms of nicotine replacement therapies (NRTs), a segment of smokers are not successful in their attempts to quit. An effective strategy for reducing the adverse effects of cigarette smoking for these two groups has been deficient.

A recent report issued by the Institute of Medicine (IOM) of the National Academy of Sciences, at the request of the U.S. Food and Drug Administration, has laid the foundation for a potential remedy to the current impasse. The resulting 656-page report titled *Clearing the Smoke: Assessing The Science Base For Tobacco Harm Reduction* (IOM Report), expresses an urgent public-health need for Potential Reduced-Exposure Products ("PREPs"), especially cigarettes (Institute of Medicine, Washington, D.C.: National Academy Press, 2001).

The first conclusion of the IOM Report is that: "For many diseases attributable to tobacco use, reducing risk of disease by reducing exposure to tobacco toxicants is feasible. This conclusion is based on studies demonstrating that for many diseases, reducing tobacco smoke exposure can result in decreased disease incidence with complete abstinence providing the greatest benefit." (IOM Report Executive Summary, pg. 4).

PREPs are therefore a public-health policy necessity when considering all economic and political dynamics. The marketing and regulation of science-based PREPs needs to be included as part of any complete public-policy strategy on tobacco. The overall goal of reducing tobacco use, including reasonable tobacco marketing restrictions to adults, strict enforcement of sales and marketing to children, and education on the harmful effects of smoking, should go hand-in-hand with the availability of PREPs to consumers to reduce tobacco's overall toll on society.

Cigarette smoke is made up of two phases: a particulate phase, which is commonly called "tar" or total particulate matter; and a vapor phase, which contains gases and semi-volatile compounds. A common definition for "tar" is "nicotine-free dry smoke" or "nicotine-free dry particulate matter" (NFDPM). More specifically, "tar" is the total particulate matter isolated from smoke, excluding water and alkaloid compounds, including but not limited to nicotine. Approximately four-fifths of the weight of tobacco smoke is made up of ambient air, which includes carbon monoxide, carbon dioxide, water, hydrogen, methane, nitrogen and oxygen. The remaining one-fifth comprises the particulate phase and semi-volatile compounds. Tar makes up less than ten percent of the weight of cigarette smoke. Yet it is the tar component that contains the majority of the most harmful compounds.

Cigarette smoke is an extremely complex mixture of chemical compounds. Years of chemical analysis of cigarette smoke have demonstrated upwards of 6000 components (tar plus gases). Approximately 4800 compounds have been identified in the tar portion of cigarette smoke (Green and Rodgman, Recent Advances in Tobacco Science, 22:131-304, 1996). Analytical methods combined with sensitive biological assays have led to the identification of 69 carcinogens in tobacco smoke (The Changing Cigarette: Chemical Studies and Bioassays, Dietrich and Ilse Hoffman, Chapter 5, Smoking and Tobacco Control Monograph No. 13, NIH Pub. No. 02-5074, October 2001).

It has become clear to researchers, however, that not all components of cigarette smoke have equal toxicity. Notably, the first U.S. Surgeon General's report on smoking in 1964 came to the conclusion that nicotine was probably not toxic at the levels inhaled by smokers, with the implication that the source of the primary pharmacologic reward to smokers was not of immediate concern (Gori, p. 3, *Virtually Safe Cigarettes—Reviving an Opportunity Once Tragically Rejected*, 2000). In fact, the Surgeon General's report indicated, "There is no acceptable evidence that prolonged exposure to nicotine creates either dangerous functional changes of an objective nature or degenerative diseases" (U.S. Surgeon General Report 1964, pg. 74). Indeed, the U.S. Food and Drug Administration now allows the sale of nicotine patches and chewing gums as smoking cessation devices that may contain more nicotine than a pack of cigarettes.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine (J. C. Leffingwell, Chapter 8 Leaf Chemistry, Tobacco: Production, Chemistry and Technology, pg. 275, 1999). Minor tobacco alkaloids include nicotine-n-oxide, N-methyl anatabine, N-methyl anabasine, pseudooxynicotine, 2,3 dipyridyl and others ("Biosynthesis and Metabolism of the Tobacco Alkaloids", Edward Leete in *Alkaloids: Chemical and Biological Perspectives, Volume I*, S. William Pelletier, Ed. 1983). Some of nicotine's common effects in humans are increased blood pressure and heart rate and improvements in concentration and short-term memory. Nicotine analogs and compounds are the subject of much recent research since they show promise in treating some diseases such as Alzheimer's and Parkinson's. Other tobacco alkaloids have similar but reduced activity compared to nicotine.

The most common measurements of cigarette smoke deliveries are reported as tar and nicotine. Tar and nicotine yields of cigarettes are shown in all consumer cigarette advertisements in the United States and numerous other countries. In many countries, yields (per cigarette) for tar, nicotine and even carbon monoxide are required to be printed on cigarette packaging. During the past several decades, cigarette design innovations have focused largely on tar and nicotine yield reductions, based on a belief embraced by the U.S. Surgeon General and the public health community that "less ought to be better" (See FIG. 1).

In the United States, tar, nicotine, and carbon monoxide yields are obtained using the Federal Trade Commission (FTC) smoking-machine test method, which defines the measurement of tar as that material captured by a Cambridge pad when a cigarette is machine smoked, minus nicotine and water (Pillsbury, et al., 1969, "Tar and nicotine in cigarette smoke". *J. Assoc. Off. Analytical Chem.*, 52, 458-62). Specifically, the FTC cigarette-testing method collects smoke samples by simulating puffing volumes of 35 ml of cigarette smoke for two seconds every 58 seconds, with none of the filter ventilation holes blocked (if any), until the burn line reaches the tipping paper plus 2 mm, or a line drawn 23 mm from the end of a non-filter cigarette. This FTC smoking-machine test method has been used in the United States since 1967 to determine smoke cigarette yields for tar and nicotine. The determination of carbon monoxide yields in cigarette smoke was added to this method in 1980.

In 1967, when the FTC introduced its testing method, it issued a news release and explained that the purpose of the testing "is not to determine the amount of tar and nicotine inhaled by any human smoker, but rather to determine the amount of tar and nicotine generated when a cigarette is smoked by a machine in accordance with the prescribed method." Nevertheless, the method serves an important role in providing an accurate way to rank and compare cigarettes according to tar, nicotine and carbon monoxide yields.

The International Standards Organization (ISO) developed a very similar smoking-machine test method for tar, nicotine, and carbon monoxide yields of cigarettes (ISO, 1991 "Cigarettes—determination of total and nicotine-free dry particulate matter using a routine analytical smoking machine" ISO: 4387:1991).

The FTC and ISO smoking methods differ in the following eight areas.

The FTC method specifies laboratory environmental conditions of 75° F.±1° F. (23.8° C.±1° C.) and a relative humidity of 60%±2% for both the equilibration and testing. The time of equilibration is a minimum of 24 hours and a maximum of 14 days. This is compared to the ISO specifications of 22° C.±1° C. and 60%±2% relative humidity for equilibration, 22° C.±2° C. and 60% relative humidity±5% for testing. The equilibration time is a minimum of 48 hours and a maximum of 10 days.

The FTC defines the cigarette butt length as a minimum of 23 millimeters or the tipping paper plus three millimeters whichever is longer. ISO defines butt length as the longest of 23 millimeters or tipping paper plus three millimeters or the filter plus eight millimeters. Both methods specify a 23-millimeter butt length for non-filter cigarettes.

ISO defines the position of the ashtray at 20-60 millimeters below the cigarettes in the smoking machine. FTC does not specify a position.

ISO specifies a two-piece snap together reusable filter holder. This filter holder contains the Cambridge pad and uses a synthetic rubber perforated washer to partly obstruct the butt end of the cigarette. The FTC method defines the use of a Cambridge filter pad but does not specify a filter pad holder assembly.

The ISO method specifies airflow across the cigarettes at the cigarette level. FTC specifies the use of a monitor cigarette to adjust airflow.

The ISO procedure defines the process of wiping the excess total particulate matter (TPM) out of the used filter holder. The inner surfaces of the filter holder are wiped with two separate quarters of an unused conditioned filter pad. The FTC method uses the backside (the side opposite of the trapped TPM) to wipe the inner surface of the filter holder.

ISO specifies using 20 ml per Cambridge pad of extraction solution to analyze nicotine and water in TPM. The FTC procedure defines 10 ml per Cambridge pad.

ISO defines the internal standards for the gas chromatographic determination of nicotine and water. The FTC procedure does not specify the internal standards.

These differences typically result in slightly lower measured deliveries for the ISO Method versus the FTC Method. The measured values between FTC and ISO methods are within the detection limits of the test or about no greater than 0.4 mg tar and about 0.04 mg nicotine for cigarettes that yield over about 10 mg.

The primary criticism of the FTC/ISO smoking-machine test methods ("FTC/ISO Method" or "FTC or ISO Method")

is that they do not accurately predict an individual smoker's level of exposure to tar, nicotine or carbon monoxide from smoking a particular cigarette National Cancer Institute Smoking and Tobacco Control Monograph 13, "Risks Associated with Smoking Cigarettes with Low Machine-measured Yields of Tar and Nicotine). These methods obtain test results under standardized conditions. However, an individual's smoking behavior may, and in most cases does, vary widely from how these standardized machines smoke cigarettes.

A human smoker may be exposed to extremely different levels of tar, nicotine and carbon monoxide per cigarette (for the exact same brand style of cigarettes) compared to the values derived from the FTC/ISO Method depending on various factors, including the smoker's frequency of puffs and volume of the inhalation of such puffs, duration of the smoke inhalation being held before exhaling, number of cigarettes smoked within a specified time period, and the percentage of the cigarette that is smoked (how far down the cigarette is smoked).

Two people that smoke the exact same cigarette brand style and the same number of daily cigarettes may not necessarily be exposed to the same levels of tar, nicotine, and carbon monoxide. Furthermore, an individual smoker is exposed to different per cigarette levels of tar, nicotine and carbon monoxide at different times. For instance, if a smoker is on a transatlantic flight and has not had a cigarette for 8 hours, he or she will most likely smoke the next cigarette very aggressively and be exposed to higher levels of tar, nicotine, and carbon monoxide than his or her per cigarette average. On the other hand, if a smoker has had many more cigarettes than usual over a brief time period, subsequent cigarettes may be smoked less aggressively, thereby exposing the smoker to less tar, nicotine, and carbon monoxide (on a per cigarette basis) than average for that smoker. Other factors, including stress, affect how often and how aggressively people smoke. Stress generally increases a smoker's nicotine consumption (IOM Report p. 254).

Filtered cigarettes can be designed to yield less tar, nicotine, and carbon monoxide according to the FTC/ISO Method. This can be accomplished by reducing the yields of these smoke fractions per puff. It is known that lower-tar, lower-nicotine and lower carbon monoxide cigarettes may be obtained by incorporating any one or more of the following modifications ("Cigarette Design", Lynn T. Kozlowski, et al., NCI Monograph 13, Chapter 2, pg. 15):

Making the filter more efficient so that it filters out more of the smoke;
Using higher porosity cigarette paper;
Putting or increasing the number of ventilation holes (including increasing their size) around the filter-tipping material so that when the smoker draws on the cigarette more air comes into the smoke mixture, thereby diluting the amount of smoke inhaled;
Increasing the cigarette burn rate with chemical additives in the cigarette paper or filler;
Using a higher percentage of reconstituted sheet tobacco made from tobacco scraps including tobacco stems and dust;
Using expanded tobacco, which creates less tar and nicotine per cigarette since less mass of whole leaf tobacco fills the cigarette rod;
Reducing the diameter of the cigarette thus reducing the weight of the filler; and
Increasing tipping paper length which changes the butt length.

FIG. 1 puts these methods in a historical perspective and shows the resulting decreases in tar and nicotine yields.

"Reconstituted tobacco" ("recon") is an important part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

"Expanded tobacco" is another important part of tobacco filler which is processed through expansion of suitable gases so that the tobacco is "puffed" resulting in reduced density and greater filling capacity. It reduces the weight of tobacco used in cigarettes. Advantageously, expanded tobacco reduces tar, nicotine and carbon monoxide deliveries and finds use, for example, in making low tar, low nicotine, and low carbon monoxide delivery cigarettes.

Nicotine content and, to a lesser extent, the tar level that cigarette smoke produces, also depends on the type and variety of tobacco used to produce the cigarette. The three types of tobaccos generally used in American brands of cigarettes are flue-cured, burley and oriental. Mixing these produces what has been referred to as "American blend" cigarettes. Generally, burley has the highest level of nicotine, followed by flue-cured and oriental. Most varieties of cured tobacco at fifteen percent moisture contain about one to three percent nicotine by weight. The alkaloid content in finished cigarettes is less than the amount in the freshly harvested tobacco leaf used to make cigarettes because losses occur during the curing, storing and manufacturing processes.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. "Flue-cured tobacco" refers to a method of drying tobacco plants in a ventilated barn with heat and is characterized by a unique color, high reducing sugar content, medium to heavy in body and exceptionally smooth smoking properties (Bacon, E. W., Wenger, R. & Bullock, J. F. (1952), Chemical changes in tobacco during flue-curing, Ind. Eng. Chem., 44, 292).

It is known that by varying the design of any of the components of the cigarette rod, as discussed above—for virtually all commercialized tobacco fillers—the levels of tar and nicotine that are measured by the FTC/ISO Method can be varied for a filtered cigarette from approximately 1 mg of tar and 0.05 mg of nicotine to approximately 20 mgs of tar and 1.8 mgs of nicotine.

When cigarettes are designed to be "lighter," tar, nicotine, and carbon monoxide levels, as measured by the FTC/ISO Method, are reduced at slightly different rates. Nevertheless, the level of tar and carbon monoxide are not reduced by any sizable percentage without a corresponding reduction in the level of nicotine by approximately the same percentage and vice versa. Even though tar and nicotine yields per the FTC/ISO Method have been reduced over the last fifty years, the "tar-to-nicotine yield ratio" ("TNR") of cigarettes has remained quite stable, as indicated in FIG. 1 and FIG. 2.

The term "cigarette" as used herein is defined as the "rod" plus, the "filler". The cigarette "rod" includes the cigarette paper, filter, plug wrap (used to contain filtration materials), tipping paper that holds the cigarette paper (including the filler) to the filter, and all glues that hold these components together. The only components of the rod of a "non-filter cigarette" are the cigarette paper and glue that seals it. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette). The term "cigarette" as used herein is also defined as (A) any roll of tobacco wrapped in paper or any other substance not containing tobacco, and (B) any roll of tobacco wrapped in any substance containing tobacco which, because of its appearance, the type of tobacco used in the filler, or its packaging and labeling, is likely to be offered to, or purchased by, consumers as a cigarette described in subparagraph (A) (1967 Federal Cigarette Labeling And Advertising Act, U.S. FTC).

The terms "non-filter rod," "full-flavor rod," "light rod" and "ultra-light rod" as used herein are defined as a non-filter cigarette minus its filler, a full-flavor cigarette minus its filler, a light cigarette minus its filler, and an ultra-light cigarette minus its filler, respectively.

As used herein, the "tar-to-nicotine yield ratio" or "TNR" of a cigarette is calculated by dividing the tar yield by the nicotine yield, both of such yields being measured by the FTC or ISO Method.

Cigarette brands in the United States and throughout most of the world are differentiated by categories such as full-flavor, lights, and ultra-lights. These designations usually appear on cigarette packs and advertising. Such categories convey cigarette strength, which is a function of the level of tar and nicotine measured by the FTC or ISO Method. Stronger-tasting or full-flavor cigarettes have higher tar and nicotine yields. The categories or "strength" of cigarettes that are generally recognized in the United States as per the FTC Method are the following:

"full-flavor cigarette" (15 mg or more tar per cigarette)
"light cigarette" (7 to 14 mg tar per cigarette)
"ultra-light cigarette" (6 mg or less tar per cigarette).

Consumer decisions on whether to smoke full-flavor versus light cigarettes based solely on tar and nicotine levels derived from the FTC/ISO Method are problematic ("Public Understanding of Risk and Reasons for Smoking Low-Yield Products", Neil Weinstein, NCI Monograph 13, Chapter 6). Since humans and smoking machines smoke cigarettes differently, the consumer may have high expectations for a cigarette reported to have low-tar ("Consumer Perception of Cigarette Yields: Is the Message Relevant?", Gio Gori, *Regulatory Toxicology and Pharmacology* volume 12, 64-68 1990). The smoker should not mistakenly believe that switching from full-flavor cigarettes (Marlboro® full-flavor produce 15 mg tar and 1.1 mg nicotine) to light cigarettes (Marlboro® lights yield 11 mg tar and 0.8 mg nicotine) will necessarily reduce the risks associated with smoking.

When light cigarette smokers are compared to full-flavor cigarette smokers (and ultra-light smokers compared to light smokers and ultra-light smokers compared to full-flavor smokers), and/or when an individual smoker who usually smokes full-flavor or light cigarettes switches to reduced yield cigarettes, or occasionally smokes reduced yield cigarettes, some or all of the following smoking behaviors may occur to some extent:

More puffs taken per cigarette;
Larger individual puffs or puff volume (e.g., 55 ml of smoke may be consumed versus 35 ml);
Variation in the duration of individual puffs (e.g., 4 seconds versus 2 seconds), therefore producing hotter cone temperatures, which have been associated with increased smoke mutagenicity*;
Holding smoke in the lungs for a longer duration before exhaling;
Deeper inhalation into the lungs;
Light cigarette smokers may block filter vent holes with fingers and lips; and
Smoking more cigarettes over a given period of time

*("Effect of pyrolysis temperature on the mutagenicity of tobacco smoke condensate", White, J. L., et al., *Food and Chemical Toxicology* 39, pg. 499-505 (2001)). As stated in the IOM Report: "In order to maintain the desired intake of nicotine, many smokers who changed to low-yield products also changed the way they smoked in the manner previously described. Thus, their exposure to tobacco toxicants is higher than would have been predicted by standardized assays and people who have continued to use these products have not significantly reduced their disease risk by switching to them" (IOM Report p. 2).

Differences in smoking behavior observed among smokers of full-flavor, light, and ultra-light cigarettes have been collectively called "compensation" ("Compensatory Smoking of Low Yield Cigarettes", Neal Benowitz, NCI Monograph 13). "Compensation" is smoking more intensively due to the reduced presence of nicotine in tobacco smoke. Smokers compensate by smoking lower-yield cigarettes (versus higher-yield cigarettes) more aggressively in order to obtain their desired nicotine impact and mouth feel of smoke, which are important sensory properties (Jed E. Rose, "The role of upper airway stimulation in smoking," Nicotine Replacement: A Critical Evaluation, p 95-106, 1988).

The Wilcox group has concluded that smokers who switch to lower-tar and nicotine cigarettes compensated by increasing their cigarette consumption per day compared to a control group. Data pooled from four cohorts failed to show a statistically significant benefit for low-tar cigarettes in terms of lung cancer risk, even among different levels of smoking (Tang et al., 1995b), as did another large cohort study (Sidney et al., 1993). Lee and Garfinkel provided a summary of lung cancer risk and type of cigarette smoked (Lee and Garfinkel, 1981) and were unable to demonstrate a significant decrease in risk based on tar content (IOM Report p. 401). Recent increases of adenocarcinomas in lower airways of smokers are hypothesized to be due to so-called smoking compensation of low-yield products. Smokers of these products inhale more deeply to increase their nicotine dose (IOM Report p. 285).

Consequently, the three-decade consumer trend towards "lighter" cigarettes may not have been beneficial to smokers' health. Generally, by compensation, smokers of light cigarettes inhale just as much tar and nicotine as full-flavor smokers. Of course, light cigarettes do taste differently than full-flavor cigarettes and these taste differences are usually why most smokers choose the brands styles that they do. However, in the U.S. alone, there are currently millions of smokers of light and ultra-light cigarettes that have switched from higher yielding cigarettes.

FIG. 2 shows tar and nicotine yields from the FTC Method for some American brand styles. "Brand style(s)" are different versions or styles of cigarettes within a brand family (e.g., Marlboro® ultra-lights kings filter box). FIG. 2 also shows the resulting TNRs of such brand styles. Whether the brand styles are king size (usually 85 mm in length), 100's (100 mm in length), full-flavor, lights, or ultra-lights, their resulting TNRs are relatively close in value. Ultra-lights tend to have somewhat lower TNRs, mainly due to the fact that the extra ventilation in the design of such cigarettes lowers yields (from the FTC/ISO Method) of tar at a slightly higher rate than nicotine. The simple average TNR of FIG. 2 is 14.22.

The sales weighted average of tar and nicotine yields for the 1998 FTC report was 12.0 mg tar and 0.88 mg nicotine, which gives a TNR of 13.64. FIG. 1 demonstrates that in 1950 the average TNR was about 14.44 (about 39 mg tar/about 2.7 mg nicotine). These numbers demonstrate that the average TNRs of American cigarettes from about 1950 to the present have been fairly consistent.

The 1998 FTC Report was released in 2000, covering the cigarette brands of 1998, and was the last year that the FTC chose to publicly release tar, nicotine and carbon monoxide yields from cigarettes. Out of the 1294 cigarette brand styles evaluated, only 3 have a calculated TNR below 8. In fact, only a total of 8 brand styles have calculated TNRs of less than 10. These consist of 1 Rothmans®, 3 Canadian Players®, 2 Old Gold®, 1 Now®, and 1 Carlton®. While only the tar, nicotine and carbon monoxide numbers were listed in the report, TNRs can be easily calculated from these numbers by dividing the yield of tar by the yield of nicotine. Two other Carlton® brand styles have yields of <0.5 tar and 0.1 nicotine. Since the actual raw numbers of the tar yields can not be determined and since there is an enormous impact due to rounding at these levels, the numbers for these 2 brand styles do not appear to reflect the prior art.

2 of the 3 brand styles with TNR's of less than 8 (Carlton® 100 filter soft pack and Now® king filter soft pack) were reported in the 1998 FTC Report to yield 1 mg tar and 0.2 mg nicotine, thereby having a TNR of 5. However, the TNRs of these 2 brand styles are mainly due to the nature of rounding small numbers. From the 1998 FTC report, "Tar and carbon monoxide ratings are rounded to the nearest milligram (mg.); those with 0.5 mg or greater are rounded up, while those with 0.4 mg or less are rounded down. The nicotine figures are rounded to the nearest tenth of a milligram. Those with 0.05 mg or greater are rounded up; those with 0.04 mg or less are rounded down." Therefore, an ultra-light cigarette delivering 1.4 mg of tar and 0.15 mg nicotine would be reported as 1 mg tar and 0.2 mg nicotine (TNR of 5), even though the actual TNR would equal 9.33. Cigarettes delivering 1 mg of tar and 0.1 mg nicotine have low consumer acceptability due to smoke thinness (lack of taste) and too much draw resistance. In 2000, the market share of cigarette brand styles that yielded 1-3 mg tar pursuant to the FTC Method had a U.S. market share of only 1.3 percent. Ninety-two percent of the brand styles yielding 3 mg tar or less tar printed their FTC tar and nicotine ratings on their packs. This contrasts to brand styles that yielded 12 or more mg tar, in which only 0.01 of one percent printed their FTC tar and nicotine rating on their packs (FTC Cigarette Report for 2000, 2002, p. 15).

Further evidence that the FTC's rounding procedure is responsible for these 2 brand styles' TNRs of 5 in the 1998 FTC Report and do not appear to accurately reflect prior art is that the hard pack version of the Carlton® 100 filter soft pack brand style lists a rating of 1 mg tar and 0.1 mg nicotine (TNR of 10). It can be inferred that the "0.2" mg nicotine rounded number for the soft pack version was in reality close to 0.15 mg nicotine-in raw number terms. Similarly, the menthol version of the Now® king filter soft pack has a listed rating of 1 mg tar and 0.1 nicotine, which also means that the "0.2" nicotine rounded number for the non-menthol version was most likely close to 0.15 mg nicotine-in raw number terms. Also, the exact Carlton® (100 filter soft pack) brand style that is listed in the 2000, 2001, and 2002 FTC reports yields 1 mg tar and 0.1 mg nicotine (TNR of 10), not the 1 mg tar and 0.2 mg nicotine (TNR of 5) as listed in the 1998 FTC report.

10 out of the 12 brand styles (out of the 1294 total) that yield 1 mg tar also yield 0.1 mg nicotine (TNR of 10). The other 2 have been discussed above (Carlton® 100 filter soft pack and Now® king filter soft pack). The FTC's rounding procedure on the tar side may, and most likely does, contribute to reduce the TNRs of these 2 very low-yielding brand styles. It is likely that manufacturers target the yields of these 1 mg tar brand styles at about 1.4 mg tar and 0.14 mg nicotine, which is a balance of being able to advertise the 1 mg tar level on the brand's packaging and the negative taste considerations of having the cigarettes actually yield (without rounding) 1 mg tar or lower. This is most likely why extremely similar brand styles (hard pack as opposed to soft pack and menthol as opposed to non-menthol) go one way or another (having a TNR of 5 versus 10) due to rounding. Thus, these 2 brand styles do not appear to reflect the prior art.

The third brand style that has a TNR of lower than 8 in the 1998 FTC report was Old Gold® non-filter hard pack, which has a TNR of 5.55 (10 mg tar and 1.8 mg nicotine). This listing for a non-filter brand style appears erroneous. There are 72 non-filter brand styles listed in the 1998 FTC report. The lowest TNRs of these, after the Old Gold® non-filter hard pack, is English Ovals® non-filter, hard pack, which has a TNR of 13 (26 mg tar and 2.0 mg nicotine). In fact, the lowest tar yield of the non-filter group of 72, besides the Old Gold® non-filter hard pack, is Picayune® regular, non-filter soft pack full-flavor. This brand style's yield is 18 mg tar and 1.2 mg nicotine (a TNR of 15).

Due to a freedom of information request to the FTC, in October, 2003 the FTC released similar reports for the years 1999-2002. The Old Gold® non-filter hard pack brand style was not included in any one of the FTC's reports for these four years or in the 1997 FTC Report. The only Old Gold® non-filter brand style that is listed in these 5 FTC Reports (1997, 1999, 2000, 2001 and 2002) is Old Gold® non-filter soft pack, which yields 25 mg tar and 1.8 mg nicotine (TNR of 13.8) in 1997, 26 mg tar and 1.9 mg nicotine (TNR of 13.68) in 1999, 27 mg tar and 1.9 mg nicotine (TNR of 14.2) in 2000, 27 mg tar and 2.0 mg nicotine (TNR of 13.5) in 2001. There is no reason for the soft pack non-filter brand style to yield substantially (or even negligible) different levels of tar than a hard pack brand style. No Old Gold® brand styles were listed in 2002 FTC Report.

For the 2002 FTC Report, only the following 4 brand styles, out of 1250, have calculated TNRs of less than 8:
  Merit® king filter ultima: 1 mg tar, 0.2 nicotine (TNR of 5);
  Now® king filter menthol soft pack, ultra-light: 1 mg tar, 0.2 nicotine (TNR of 5);
  Now® king filter soft pack, ultra-light: 1 mg tar, 0.2 nicotine (TNR of 5);
  Now® 100 filter soft pack, ultra-light: 2 mg tar, 0.3 nicotine (TNR of 6.66).

There is also another exact same brand style listed as Merit king filter ultima, yet this one yields 1 mg tar and 0.1 mg nicotine (TNR of 10). It is believed that the low TNRs of these brand styles are such for the same reasons as listed in the 1998 FTC report, and do not appear to accurately reflect the prior art. Only a total of 5 brand styles (out of 1250) have calculated TNRs of greater than 8 and less than 10 in the 2002 FTC report. These consist of 3 Canadian Players®, 1 Carlton®, and 1 other Merit®.

The recent trend in cigarette PREPs is reducing selected carcinogens in tobacco smoke. Two cigarette PREPs that have recently been introduced in the United States: Advance®, manufactured by Brown & Williamson Tobacco Company, and Omni®, manufactured by Vector Tobacco, Inc. Advance® achieves reductions of tobacco-specific nitrosamines (TSNAs) with patented (See U.S. Pat. Nos. 5,803,081, 5,845,647, 6,135,121, 6,202,649, 6,311,695, 6,338,348, 6,350,479, 6,425,401, RE38,123, and 6,569,470) and patent-pending (See U.S. Publication Nos. 20020174874 and 20030018997) tobacco leaf curing technologies in conjunction with specialized filtration technology.

Omni® reduces polycyclic aromatic hydrocarbons (PAHs), TSNAs, and catechols by using a palladium catalytic system (See U.S. Publication No. 20030000538) added to the filler and activated charcoal filtration. Omni®, king size full-flavor has 15 mg tar and 1.0 mg of nicotine (TNR of 15). Advance® lights king box has 10 mg tar and 0.8 mg of nicotine (TNR of 12.5).

A major dilemma in designing a PREP is that years of clinical studies may be required to understand the reduced risks, if any, of a PREP compared to conventional cigarettes. This is especially true of PREPs, similar to Advanced and Omni® that do not reduce whole tobacco smoke deliveries but only reduce some chemical compounds in tobacco smoke.

Polycyclic aromatic hydrocarbons (PAHs) are the result of the incomplete combustion of lipids and terpenes found naturally in tobacco. The scientific community considers these compounds to be potent carcinogens in tobacco smoke. Tobacco-specific nitrosamines are formed during the tobacco curing process and during smoking (Hoffman, D., Dong, M., & Hecht, S. S. (1977), Origin in tobacco smoke of N-nitrosonornicotine, a tobacco-specific carcinogen. Brief communication, J. Natl. Cancer Inst., 58, 1841-4). These are also considered potent carcinogens. TSNAs are formed by a reaction between a nitrosating agent and alkaloids found naturally in tobacco and are also carcinogens in tobacco smoke. (U.S. Publication No. 20040144397).

Even with reductions in these potent carcinogens, many other carcinogens in tobacco smoke are still present, which these technologies do not address. Also, many other compounds that may not cause cancer but are detrimental to other aspects of human health, such as cardiovascular and respiratory diseases, are not reduced.

Eclipse® and Accord® provide a smoking experience as close as possible to smoking a conventional cigarette but with minimal or no combustion (pyrolysis) of the tobacco. The intended advantage of these products is a significant reduction in the formation of compounds resulting from the combustion of tobacco in conventional cigarettes. These compounds are generally accepted as harmful to smokers. Since these two brands do not smoke like conventional cigarettes, they have not been very accepted by the market.

The smoking experience in both of these products relies on the following concepts. The smoke aerosol in both products is formed by heating tobacco materials containing a high content of glycerin rather than combusting the tobacco. Glycerin when heated, rapidly vaporizes, forming an inhaleable aerosol very similar in appearance and feel to cigarette smoke. Further, the heating of the tobacco materials contained in these products will release volatile flavors indigenous to the tobacco as well as nicotine. Any added tobacco volatile flavorings could be released into the smoke aerosol as well.

Eclipse® and Accord® use different methods of applying heat to the tobacco materials contained in their respective products. Accord® relies on a device known as a lighter that contains batteries, circuitry and heaters that will apply heat to a cigarette inserted into the device. It is designed in such a fashion as to deliver six puffs per cigarette inserted into the device. Cigarettes specifically manufactured for this device must be used for proper performance.

Eclipse® relies a combustible carbon tip that, when ignited, provides a source of heat to form a smoke aerosol from the tobacco materials contained in the product. The Eclipse® product has a appearance similar to a conventional cigarette, except that it is not consumed to ashes as compared to a conventional cigarette.

Both of these products pose challenges when attempting to determine the tar and nicotine delivery via the FTC method. The butt length determination is meaningless as neither product is consumed as it is puffed. The number of puffs on each product is limited by nature of their design. With Eclipse® the number of puffs is regulated by the carbon heat source. Accord® is electronically limited to six puffs. Finally, Accord® is not "lit" as prescribed by the FTC method.

It is known that *Nicotiana rustica*, which is high in nicotine content without being genetically modified, can be crossed with *Nicotiana tabacum* to produce a new plant (Wemsman, E. A., et al., *Principles of Cultivar Development, Volume 2, Crop, Species*, Ed. W. R. Fehr, Macmillan, New York 1987). Y-1 tobacco, which was initially and partially developed by the U.S. Department of Agriculture, is an example of this crossing. However, such a variety takes many more years to create than increased-nicotine tobacco by transgenic means. Other advantages of creating increased-nicotine tobacco by transgenic means versus plant crossing techniques is that transgenic processes can be performed on any type of commercialized tobacco (flue-cured, burley, and oriental) or cultivar (or variety) of tobacco, thereby maintaining the vast majority of the traits of the parent tobacco line before the genetic modification. Desirable commercial characteristics of a *N. tabacum* variety will be negatively affected when it is crossed with *N. rustica*.

FIG. 3 demonstrates that only 36.4 percent of all smoking-related deaths in the U.S. are caused by cancer, yet the public's perception is that cancer is the greatest detrimental health effect of smoking. In fact, cardiovascular diseases cause 42.4 percent and respiratory diseases cause 21.2 percent of such deaths. Epidemiological studies show a substantial drop in risk as the total amount of inhaled smoke decreases (U.S. Surgeon General, 1964, 1979, 1989). Since it is not know which of many toxins cause specific harmful effects, it would be beneficial to reduce whole tobacco smoke deliveries to the smoker to create an effective PREP—not just a handful of smoke constituents that are carcinogens.

The IOM report concludes that "Nicotine is one of the factors crucial to the success of a tobacco product." (p. 29). Accordingly, retaining nicotine at pleasurable levels, while reducing the more toxic components of tobacco, would be another general strategy for harm reduction (IOM Report p. 29). By reducing the dose of whole tobacco smoke that is inhaled per cigarette and/or reducing the number of cigarettes smoked per day, all carcinogens and harmful gases would be reduced by similar percentages. The most effective way to accomplish reductions in whole tobacco smoke deliveries, given a smoker's propensity to compensate, is to reduce the TNR of cigarettes. With reduced TNR cigarettes, the per-puff level of whole tobacco smoke that the smoker inhales, which includes tar and carbon monoxide, would be reduced in many cases while maintaining the smoker's required nicotine level.

According to epidemiologic evidence, risk relates linearly to the amount of cigarettes smoked. The evidence of reduced dose should be the foundation of less hazardous cigarette regulation (Gori, 2002 Coresta Congress). A "dose-response relationship" is defined as the relationship between disease-risk regression and exposure regression (e.g., the higher the dose, the greater incidence of disease). "Currently available data allow estimation, albeit imprecise, of a dose response relationship between exposure to whole tobacco smoke and major diseases that can be monitored for evaluation of harm reduction potential" (p. 9, IOM Report). Since a dose-response relationship currently exists for whole tobacco smoke, the benefits of low TNR cigarettes which can reduce whole tobacco smoke deliveries to smokers could be promptly evaluated and endorsed by public health regulators such as the U.S. Food and Drug Administration (FDA).

In FIG. 2, if the tar yield from the FTC Method for Marlboro® full-flavor kings of 15 mg is compared with the tar yield from the FTC Method for Marlboro® lights kings of 11 mg, then a 4 mg reduction of tar is observed. This might, on the surface, indicate that a smoker would inhale 4 mg less tar by switching to the light product. However, the TNR values of 13.64 and 13.75 respectively, show no improvement in switching in terms of the amount of tar inhaled per mg of nicotine per cigarette. Since compensation may occur when switching from full-flavor to light or ultra-light cigarettes and from light to ultra-light cigarettes, TNR values may provide a more accurate representation of a cigarette brand's true smoke delivery with respect to human smoking behavior.

It is well known that the motivations of smokers extend to a variety of factors such as taste, esthetic, and behavioral incentives, of which the pharmacologic rewards of nicotine are by far the most significant. With the exception of extremely low yield cigarettes, smokers in general manage to utilize an average of about 1 mg of nicotine (per cigarette) from cigarettes of any brand, regardless of the machine yields on the standard FTC smoking machine (Gori, pg. 3 Virtually Safe Cigarettes—Reviving an Opportunity Once Tragically Rejected, 2000). "The ceiling of how much nicotine a smoker inhales is about 2 mg per cigarette. The number of puffs per cigarette averages around eight. Thus a top delivery of 250 micrograms per puff would be enough to satisfy peak demands, although usually smokers will extract and inhale less than this maximum delivery" (Gori, Gio, Less Hazardous Cigarettes, Tobacco Reporter, p. 31, June, 2004).

In a British Medical Journal article (BMJ, 1976 volume 1, pp. 1430-1433) and again in a 1980 Banbury Report (#3 A Safe Cigarette, pp. 297-310), Michael Russell advocated low-tar, medium-nicotine and low-carbon monoxide cigarettes as safer alternatives to cigarettes available on the market at that time. A review of German tobacco industry research from Internet documents indicated that scientists thought a safer cigarette would have a greater ratio of nicotine to tar (lower TNR) (*Tobacco Control* 2000; 9:242-248, pg. 4).

A desirable reduced-exposure cigarette should deliver a smoker's desired level of nicotine per cigarette as cleanly and efficiently as possible while maintaining acceptable taste. In fact, "reverse compensation" may occur in a number of situations with low TNR cigarettes, since smokers inhale less whole tobacco smoke while obtaining a satisfactory amount of nicotine. "Reverse compensation" is defined as smoking less intensively due to the increased presence of nicotine in tobacco smoke.

Low TNR cigarettes would also benefit nonsmokers. By more efficiently delivering nicotine to smokers, less cigarettes per day may be smoked and less of each cigarette may be smoked, which will generate less sidestream smoke (what arises from the lit end of a cigarette, mostly between puffs) and less environmental tobacco smoke (smoke present in air, consisting of exhaled mainstream smoke and sidestream smoke). Mainstream smoke (mainstream whole tobacco smoke) is what emerges from the (smoker's) "mouth" or butt end (filter tip) of a puffed cigarette (IOM Report p. 283).

Accordingly, there is a need for low TNR cigarettes that can more efficiently deliver the physiological effect of nicotine without as much harmful tar and gases.

SUMMARY OF THE INVENTION

The present invention provides a cigarette comprising an increased-nicotine transgenic plant or plant portion of a species of the genus *Nicotiana* and having a tar-to-nicotine yield ratio (TNR) of between about 3 and about 8, as measured by the FTC or ISO method. The increased-nicotine transgenic plant or plant portion exhibits increased nicotine as compared to a non-transformed parent plant or plant portion from which the transgenic plant or plant portion is produced and contains and expresses at least one heterologous nucleic acid that up-regulates the production of nicotine in the transgenic plant or plant portion. The increased-nicotine transgenic plant or plant portion, as compared to a non-transformed control plant or plant portion, contains and expresses a heterologous DNA encoding at least a segment of an enzyme required for the biosynthesis of nicotine in tobacco, the transgenic plant or plant portion exhibiting increased levels of the enzyme as compared to a non-transformed control plant or plant portion and increased-nicotine content as compared to a non-transformed control plant or plant portion.

The enzyme may be selected from a group consisting of arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS). The plant species may be *Nicotiana tabacum*.

The cigarette may yield about 1 mg of tar and between about 0.12 mg and about 0.34 mg of nicotine, about 2 mg of tar and between about 0.25 mg and about 0.68 mg of nicotine, about 3 mg of tar and between about 0.36 mg and about 1.0 mg of nicotine, about 4 mg of tar and between about 0.5 mg and about 1.36 mg of nicotine, about 5 mg of tar and between about 0.62 mg and about 1.7 mg of nicotine, about 6 mg of tar and between about 0.75 mg and about 2.0 mg of nicotine, about 7 mg of tar and between about 0.87 mg and about 2.33 mg of nicotine, or about 8 mg of tar and between about 1.0 mg and about 2.66 mg of nicotine. The present invention also includes a cigarette comprising an increased-nicotine transgenic plant or plant portion of a species of the genus *Nicotiana*.

The invention also includes a method of making a cigarette comprising providing an increased-alkaloid transgenic plant or plant portion, as compared to a non-transformed control plant or plant portion, of a species of the genus *Nicotiana*, crossing the plant with a plant of the species *Nicotiana tabacum* to obtain a progeny plant, and producing a cigarette comprising the progeny plant. The cigarette may have a tar-to-nicotine yield ratio of between about 3 and about 8, as measured by the FTC or ISO method.

The invention also includes a method of making a cigarette comprising providing a reduced-nicotine transgenic *Nicotiana tabacum* plant or plant portion having a reduced nicotine content as compared to a non-transformed control plant or plant portion, crossing the reduced-nicotine plant with a *Nicotiana rustica* plant to obtain a progeny plant, and producing a cigarette comprising the progeny plant. The progeny plant or plant portion exhibits increased nicotine as compared to the *Nicotiana tabacum* plant from which the transgenic plant or plant portion is produced. The progeny plant may be used in a cigarette having a tar-to-nicotine yield ratio of between about 3 and about 8, as measured by the FTC or ISO method.

The invention also includes a method of making a cigarette comprising providing an increased-nicotine transgenic plant or plant portion, as compared to a non-transformed control plant or plant portion, of a species of the genus *Nicotiana*, producing reconstituted tobacco from the plant or plant portion, and producing a cigarette comprising the reconstituted tobacco. The cigarette may have a tar-to-nicotine yield ratio of between about 3 and about 8, as measured by the FTC or ISO method.

The invention also includes a method of making a cigarette comprising providing an increased-nicotine transgenic plant or plant portion, as compared to a non-transformed control plant or plant portion, of species of the genus *Nicotiana*, producing expanded tobacco from the plant or plant portion, and producing a cigarette comprising the expanded tobacco. The cigarette may have a tar-to-nicotine yield ratio between about 3 and about 8, as measured by the FTC or ISO method.

The invention also includes a cigarette comprising a transgenic plant or plant portion of a species of the genus *Nicotiana* that exhibits increased nicotine as compared to a non-transformed parent plant or plant portion from which the transgenic plant or plant portion is produced and a lower tar-to-nicotine yield ratio as compared to a control cigarette comprising the non-transformed parent plant or plant portion.

The invention also includes a method of making a cigarette comprising providing an increased-nicotine transgenic plant or plant portion, as compared to a non-transformed control plant or plant portion, of a species of the genus *Nicotiana*, extracting nicotine from the transgenic plant or plant portion, providing a plant or plant portion of a species of the genus *Nicotiana*, adding the extracted nicotine to the species to form increased nicotine plant material, producing a cigarette comprising the increased nicotine plant material. The nicotine may be nicotine salts of organic acids.

The invention also includes a method of making a cigarette comprising providing an increased-nicotine transgenic plant or plant portion, as compared to a non-transformed control plant or plant portion, of a species of the genus *Nicotiana*, extracting nicotine from the transgenic plant or plant portion, providing a second plant or plant portion of a species of the genus *Nicotiana*, adding the extracted nicotine to the second plant or plant portion to form increased nicotine plant material, producing a cigarette comprising the increased nicotine plant material and having a lower tar-to-nicotine yield ratio as compared to a control cigarette comprising the second plant or plant portion without the addition of the extracted nicotine.

The invention also includes a method of making a cigarette comprising providing a reduced-nicotine transgenic plant or plant portion, as compared to a non-transformed control plant or plant portion, of a species of the genus *Nicotiana*, producing cigarette tobacco from the transgenic plant or plant portion, adding nicotine to the cigarette tobacco, producing a cigarette comprising the cigarette tobacco and having a tobacco-specific nitrosamines level below about 0.5 micrograms per gram. The nicotine may be nicotine salts of organic acids or synthesized nicotine. The tobacco-specific nitrosamines level may be less than about 0.05 micrograms (50 ppb) per gram of tobacco and the cigarette may have a tar-to-nicotine yield ratio of between about 3 and about 8.

The invention also includes a method of making a tobacco product comprising providing a transgenic plant or plant portion of a species of the genus *Nicotiana* that exhibits reduced nicotine as compared to a non-transformed parent plant or plant portion from which the transgenic plant or plant portion is produced, producing tobacco from the transgenic plant or plant portion, adding nicotine to the tobacco, producing a tobacco product comprising the tobacco and having a lower tobacco-specific nitrosamines level as compared to a control product comprising the non-transformed parent plant or plant portion. The reduced-nicotine transgenic plant or plant portion, as compared to the non-transformed control plant or portion, may contain and express at least one heterologous nucleic acid that down-regulates the production of nicotine in the transgenic plant or plant portion. The reduced-nicotine transgenic plant or plant portion may contain and express a heterologous DNA encoding at least a segment of an enzyme required for the biosynthesis of nicotine in tobacco, the transgenic plant or plant portion exhibiting reduced levels of the enzyme as compared to a non-transformed control plant or plant portion and reduced-nicotine content as compared to a non-transformed control plant or plant portion. The tobacco-specific nitrosamines level may be below about 1 microgram per gram (1 ppm). The tobacco product may be in a form selected from a group consisting of leaf tobacco, shredded tobacco and cut tobacco and may be selected from a group consisting of snuff, pipe tobacco, cigar tobacco, chewing tobacco and cigarette tobacco.

The invention also includes a method of making expanded tobacco comprising providing an increased-nicotine transgenic plant or plant portion, as compared to a non-transformed control plant or plant portion, of a species of the genus *Nicotiana*, producing tobacco from the transgenic plant or plant portion, and expanding the tobacco.

The invention also includes a method of making reconstituted tobacco comprising providing plant material selected from a group consisting of an increased-nicotine transgenic plant or plant portion, as compared to a non-transformed control plant or plant portion, of a species of the genus *Nicotiana*, a reduced-nicotine transgenic plant or plant portion, as compared to a non-transformed control plant or plant portion, of a species of the genus *Nicotiana*, deproteinized tobacco fiber, and freeze-dried tobacco, and reconstituting the plant material.

The invention also includes a method of making reconstituted tobacco comprising providing a reduced-nicotine transgenic plant or plant portion, as compared to a non-transformed control plant or plant portion, of a species of the genus *Nicotiana*, and reconstituting the transgenic plant or plant portion. The plant species may be selected from a group consisting of *Nicotiana tabacum* and *Nicotiana rustica*. The reconstituted tobacco may further comprise reconstituted deproteinized tobacco fiber. The invention also includes a cigarette comprising such reconstituted tobacco and having a reduced TSNA yield as compared to a control cigarette comprising the non-transformed parent plant or plant portion. TSNAs as used herein may be selected from a group consisting of NNN, NNK, NAT, and NAB and the cigarette may have a reduced yield of compounds selected from a group consisting of benzo(a)pyrene, phenols, and catechols as compared to a control cigarette comprising such non-transformed parent plant or plant portion.

The invention also includes a method of making reconstituted tobacco comprising providing an increased-nicotine transgenic plant or plant portion, as compared to a non-transformed control plant or plant portion, of a species of the genus *Nicotiana*, and reconstituting the transgenic plant or plant portion. The method may further comprise freeze-drying the transgenic plant or plant portion after harvesting it.

The invention also includes methods of creating and producing novel tobacco varieties for use in low TNR cigarettes so that such cigarettes are more conducive for producing consumer acceptable products. Such varieties include combining transgenic high-nicotine traits with high reducing sugar backgrounds and transgenic high-sugar traits. Other novel varieties to increase consumer acceptability of low INR cigarettes include combining transgenic high-nicotine traits with transgenic high fatty acid traits. Such methods reduce the smoke pH of low TNR cigarettes.

The invention also includes methods of adding sugar, fatty acids, citric acid, lactic acid, and malic acid to the tobacco or the filler of low TNR cigarettes to reduce the smoke pH of such cigarettes to produce more consumer acceptable products.

BRIEF DESCRIPTION OF THE DRAWINGS

FIG. 2 is a table showing a comparison of tar and nicotine yields (as of 2003) of certain cigarette brands and their resulting TNRs.

FIG. 4 is a table that demonstrates the plant characteristics of a reduced-nicotine transgenic plant line.

DETAILED DESCRIPTION OF PREFERRED EMBODIMENTS

Figure 1:
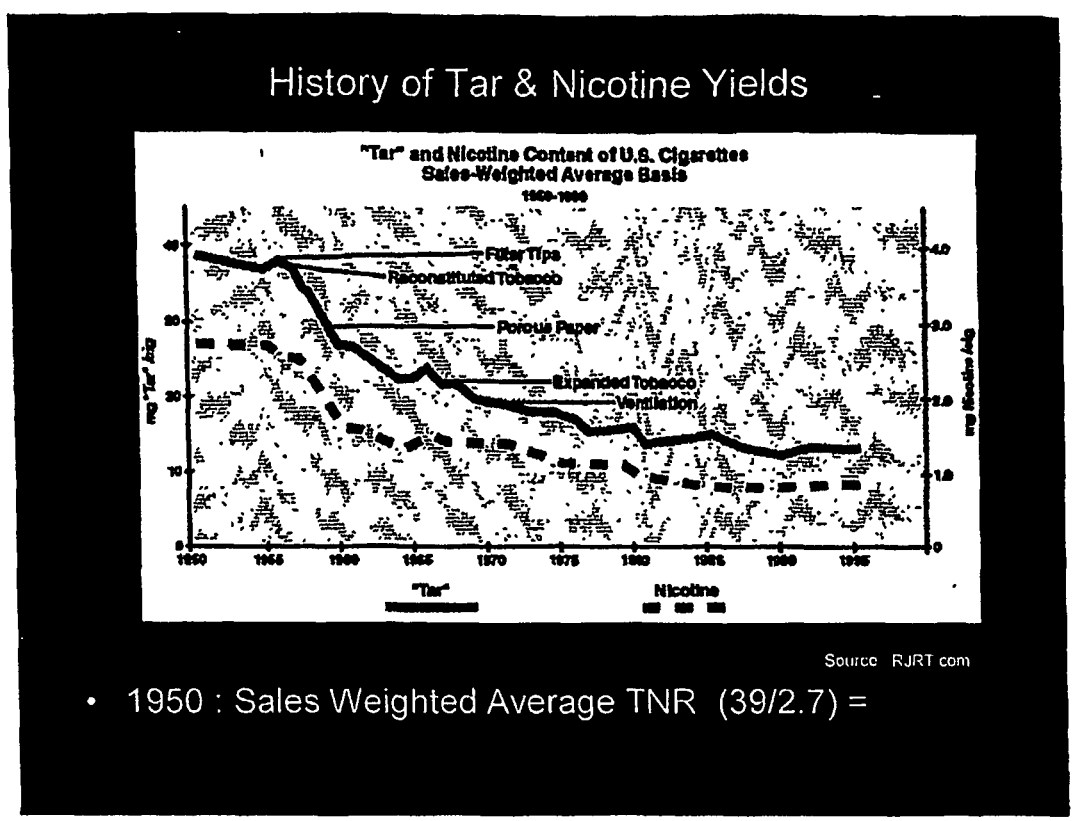
FIG. 1 is a graph showing average tar and nicotine yields of American cigarettes between 1950 and 1995.
Figure 3:
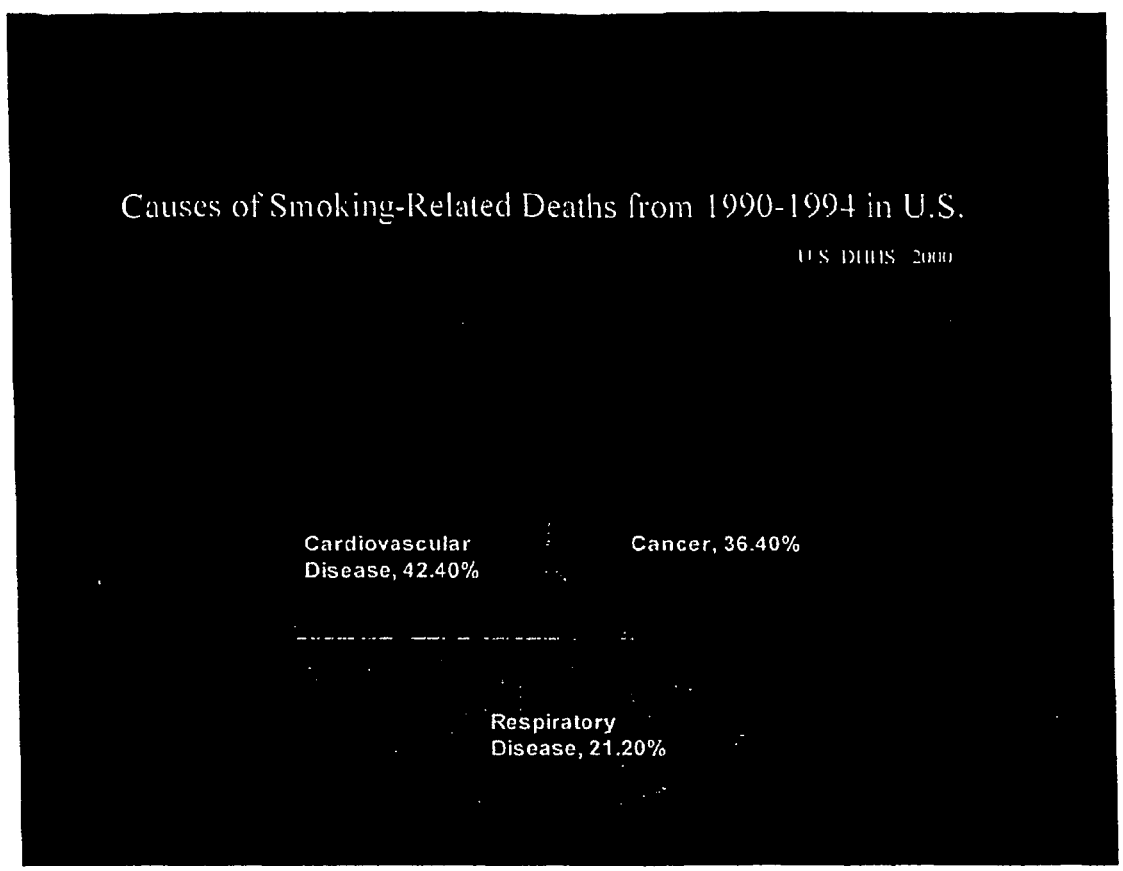
FIG. 3 is a pie chart which shows the causes of smoking-related deaths in the United States from 1990-1994.

Some aspects of the present invention reduce the tar-to-nicotine yield ratio (TNR) of cigarettes by restricting tar delivery to the smoker while providing adequate amounts of nicotine to maintain smoker satisfaction. The result is a cigarette that effectively offers smokers a satisfactory amount of nicotine with preferably less harmful tar and gases. Failure of current light and ultra-light commercial cigarettes to efficiently deliver a satisfactory level of nicotine to smokers, results in aggressive smoking behavior called compensation, which may cause more harm to the smoker. This is because such cigarettes reduce tar and nicotine yields concurrently and at about the same rate.

The present invention, in conjunction with different levels of filtration and/or smoke dilution, provides for increasing the nicotine content of the cigarette's filler, either genetically within the tobacco plant, or by adding nicotine to the filler, thereby allowing the cigarette's nicotine delivery to the smoker to be maintained, while preferably decreasing the cigarette's tar delivery.

As used herein, "increased-nicotine transgenic plant" means a recombinant (or "transgenic") tobacco plant that contains a higher nicotine content than the non-transgenic "parent" (or unmodified "control") plant from which the transgenic plant is produced.

As used herein, "increased-alkaloid transgenic plant" means a recombinant (or "transgenic") tobacco plant that contains a higher total alkaloid content than the non-transgenic "parent" (or unmodified "control") plant from which the transgenic plant is produced.

As used herein, "reduced-nicotine transgenic plant" means a recombinant (or "transgenic") tobacco plant that contains less than half, preferably less than 25%, and more preferably less than 20% or less than 10%, of the nicotine content of the non-transgenic "parent" (or unmodified "control") plant from which the transgenic plant is produced. It will be appreciated that some small level of residual nicotine, on the order of at least 1% or 5% as compared to the corresponding unmodified control plant, may remain in such transgenic plants used to carry out the present invention.

As used herein, "nicotine" ($C_{10}H_{14}N_2$) includes analogs of nicotine (unless nicotine is referenced to total alkaloid(s)), nicotine's two isomers, synthesized nicotine, and nicotine salts of organic acids.

Plants for use in the present methods are species of the genus *Nicotiana*, or tobacco, including but not limited to, *Nicotiana tabacum, Nicotiana rustica, Nicotiana glauca, Nicotiana excelsior, Nicotiana benthamiana, Nicotiana sylvestris Nicotiana clevelandii*, and *Nicotiana attenuata*. As used herein, "tobacco" means and encompasses any plant, species, crosses, or hybrids of the genus *Nicotiana*. Any strain or variety of tobacco may be used. Such tobacco plants are genetically modified to either increase or reduce the nicotine content, depending on intent, thereof as discussed in greater detail below. The term "plant" includes physical and chemical portions thereof, such as plant parts and plant extracts, hydrolysates, etc.

As used herein a "low TNR cigarette" or "low tar-to-nicotine yield ratio cigarette" of the present invention means a cigarette that contains an increased-nicotine recombinant tobacco plant or plant portion, including but not limited to nicotine from such plant or plant portions.

1. Low TNR Cigarettes (with Increased-Nicotine Transgenic Tobacco); Production of Novel Tobacco Varieties; and More Acceptable Low TNR Cigarettes Increased-nicotine transgenic tobacco plants used to carry out the first aspect of the present invention are, in general, recombinant tobacco plants that contains and express a heterologous nucleotide, the expression of which up-regulates an enzyme (such as arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS)) in the plant, and thereby increases the production of nicotine in the plant. Suitable recombinant plants are disclosed in M. Conkling et al., PCT Application WO98/56923 (published Dec. 17, 1998) and in M. Timko, PCT Application WO00/67558 (published Nov. 16, 2000). In general, the heterologous nucleotide comprises at least a segment of a nucleic acid encoding the enzyme to be up-regulated.

In this embodiment, increased-nicotine tobacco is incorporated into the filler of a cigarette to achieve a desired low TNR cigarette. With the combination of a full-flavor rod, preferably a light rod, and more preferably an ultra-light rod, increased-nicotine tobacco (that may include blends of conventional tobacco) cigarettes can now efficiently deliver the smoker's desired amount of nicotine per cigarette, while delivering less tar and harmful gases. The inventive low TNR cigarette is also achievable by using a non-filter rod, since smokers of non-filter cigarettes will still have the increased presence of nicotine, which in some cases will reduce inhalation of tar and harmful gases. A lowered TNR cigarette is therefore a major goal of the inventive PREP.

One specific embodiment utilizes an increased-nicotine recombinant plant that has increased quinolate phosphoribosyl transferase (QPRTase) expression relative to a non-transformed control plant, such recombinant plant comprising recombinant plant cells containing: an exogenous DNA construct comprising, in the 5' to 3' direction, a promoter operable in such plant cell and a heterologous DNA encoding at least a segment of a plant quinolate phosphoribosyl transferase mRNA, such heterologous DNA operably associated with such promoter, such plant exhibiting increased QPRTase expression compared to a non-transformed control plant and increased-nicotine content as compared to a non-transformed control plant.

Another embodiment may be carried out with an increased-nicotine recombinant plant that has increased putrescine N-methyltransferase (PMTase) expression relative to a non-transformed control plant, such recombinant plant comprising recombinant plant cells containing: an exogenous DNA construct comprising, in the 5' to 3' direction, a promoter operable in such plant cell and a heterologous DNA encoding at least a segment of a plant PMT mRNA, such heterologous DNA operably associated with such promoter, and with such heterologous DNA in sense or antisense orientation; such plant exhibiting increased PMT expression compared to a non-transformed control plant and increased-nicotine content as compared to a non-transformed control plant.

Still other embodiments may be carried out in like manner with the other enzymes listed above.

Nucleic acid constructs as described above may include insulator elements upstream (5' to) and/or downstream (3' to) of the construct described above, as set forth, for example, in U.S. Pat. Nos. 6,100,448 and 6,037,525 to Thompson et al. In addition, constructs as described above may include matrix (or scaffold) attachment regions upstream and/or downstream of the construct described above, as set forth (for example) in U.S. Pat. Nos. 5,773,695 and 5,773,689 to Thompson et al.

In still another embodiment, plants utilized may contain a plurality of recombinant nucleic acids that up-regulate a plurality of enzymes in the nicotine synthesis pathway. Plants described as possessing at least one recombinant nucleic acid may thus encompass those containing the plurality. The benefits of utilizing more than one recombinant nucleic acid is that nicotine or other alkaloid levels can be increased to greater levels (versus if only one such nucleic acid is utilized) and different desired alkaloid ratios (e.g., the ratio of nicotine to total alkaloids) may be accommodated, if desired.

Figure 5:
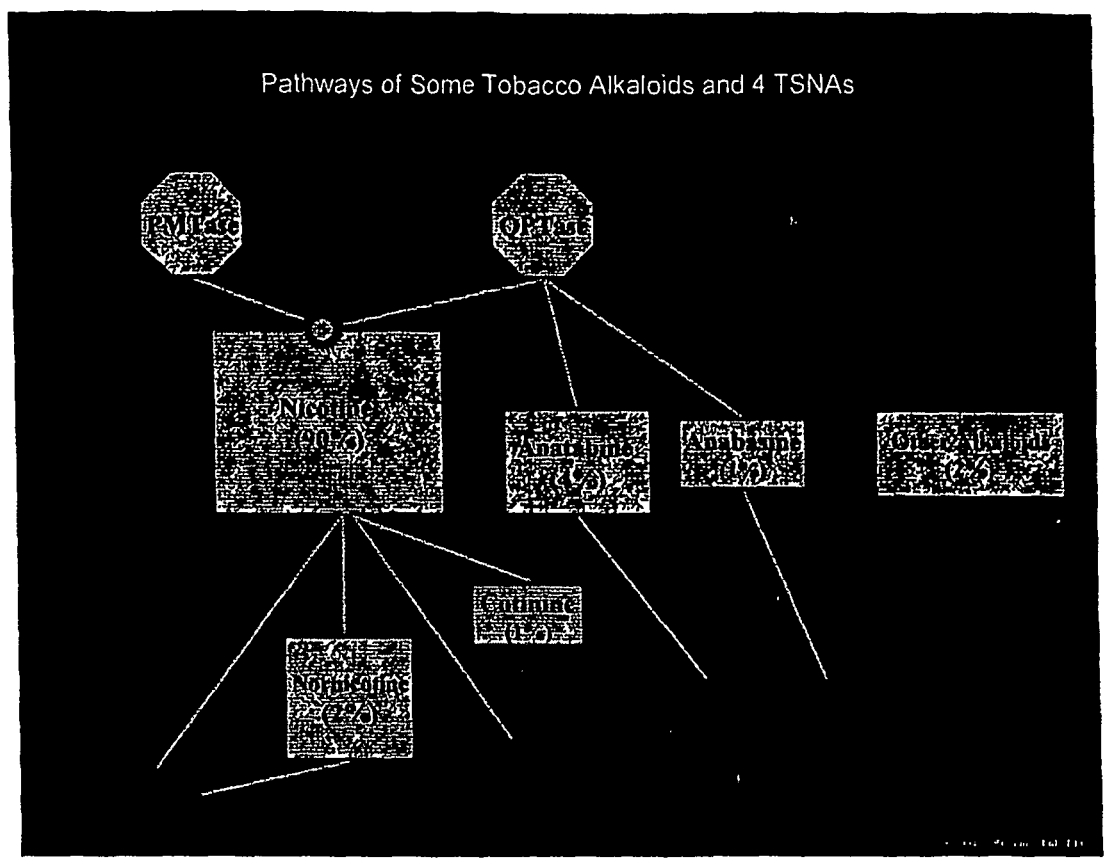
FIG. 5 is a schematic diagram of the pathways of certain tobacco alkaloids and TSNAs.
Figure 6:
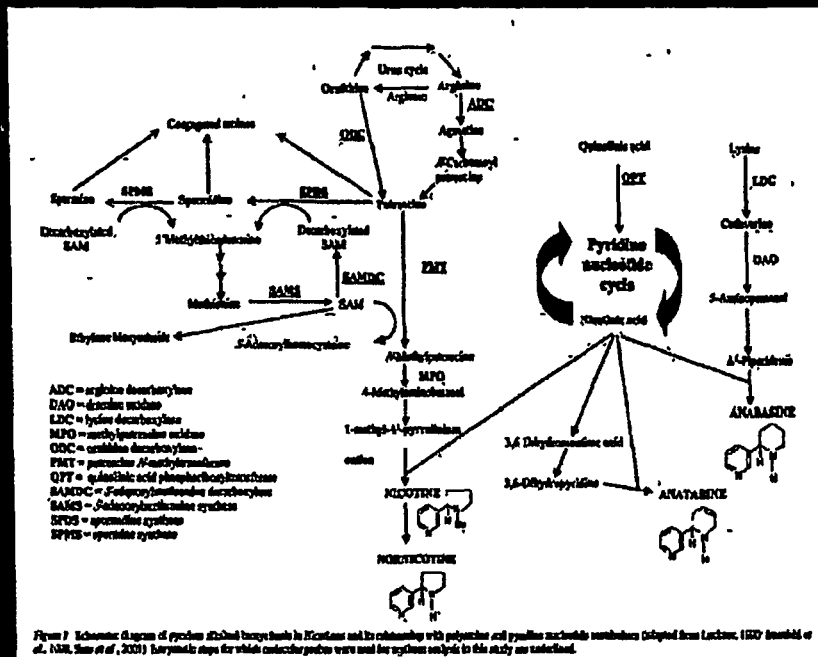
FIG. 6 is a schematic diagram of pyridine alkaloid biosynthesis in *Nicotiana* (Antisense-mediated down-regulation of putrescine N-methyltransferase activity in transgenic *Nicotiana tabacum* L. can lead to elevated levels of anatabine at the expense of nicotine; Yupynn Chintapakom and John D. Hamill; Plant Molecular Biology 53: 87-105, 2003).

In another embodiment, the same plant or cell may contain at least one recombinant nucleic acid that up-regulates an enzyme in the nicotine or alkaloid synthesis pathway, while also containing at least one recombinant nucleic acid that down-regulates an enzyme in the nicotine or alkaloid synthesis pathway. As an example, if PMT is up-regulated, and QPT is down-regulated, the nicotine to total alkaloid ratio will increase. This ratio is preferably as close to one for advantages for the prevention of the formation of NAT, NAB and possibly other TSNAs. See FIG. 5 and FIG. 6.

In another embodiment, the present invention utilizes a increased-nicotine recombinant plant that has both increased QPRT and increased PMT expression relative to a non-transformed control plant, such recombinant plant comprising recombinant plant cells containing: (i) a first exogenous DNA construct comprising, in the 5' to 3' direction, a promoter operable in such plant cell and a heterologous DNA encoding at least a segment of a plant quinolate phosphoribosyl transferase mRNA, such heterologous DNA operably associated with such promoter; and (ii) a second exogenous DNA construct comprising, in the 5' to 3' direction, a promoter operable in such plant cell and a heterologous DNA encoding at least a segment of a plant PMT mRNA, such heterologous DNA operably associated with such promoter, such plant exhibiting increased QPRT and increased PMT expression compared to a non-transformed control plant and increased-nicotine content as compared to a non-transformed control plant. As used herein, QPT, QPRT, and QPRTase are used interchangeably. PMT and PMTase are also used interchangeably.

Examples of recombinant plants that may be used to carry out these embodiments include, but are not limited to, known plants transformed with DNA encoding the tobacco quinolate phosphoribosyl transferase gene (NtQPT1) (see, e.g., PCT Application WO98/5556923 by Conkling et al.); DNA encoding tobacco putrescine N-methyltransferase, such as PMT1, PMT2, PMT3 and PMT4; DNA encoding tobacco arginine decarboxylase, such as ADC1 and ADC2; DNA encoding tobacco ornithine decarboxylase (ODC); DNA encoding tobacco S-adenosylmethionine synthetase (SAMS); DNA encoding tobacco NADH dehydrogenase; and DNA encoding tobacco phosphoribosylanthranilate isomerase (PRAI) (which are known and described in PCT Application WO 00/67558 by M. Timko et al.).

U.S. Pat. Nos. 6,423,520, 6,586,661, 5,260,205, 5,369,023, 5,668,295 and U.S. Published App. No. 20030018997 also describe methods of altering nicotine content of tobacco plants by genetically modifying either QPRT or PMT in the nicotine biosynthetic pathway.

The nicotine content of each individual transformed increased-nicotine tobacco plant, with each of the above methods, is variable. Therefore, if a tobacco plant line is desired with approximately 6.2 percent nicotine content (on a dry weight basis), it will take a reasonable number of genetic plant transformations to one skilled in the art to obtain a homozygous plant having such nicotine content.

Seeds from selfing of primary transformants that contain a single transgene locus will have three different genotypes since the transgene (that confers high nicotine) segregates 1:2:1; 25% will not carry the transgene, 50% will be heterozygous for the transgene, and 25% will be homozygous for the transgene. The progeny of the heterozygous class of seeds will again segregate 1:2:1. The homozygous class of seeds will be most useful for further propagation because 100 percent of all their progeny will carry the transgene (with two copies if plants are selfed, and one copy if the homozygous transgenic plants are crossed to a non-transgenic parent). When seeds from selfing of the homozygous progeny are planted in the field they will contain very similar increased-nicotine contents as the parent plant grown under similar climate, soil, and planting conditions.

Such genetic embodiments of producing increased-nicotine tobacco are more economical to implement in commercial increased-nicotine tobacco products than adding nicotine, or nicotine salts of organic acids, directly to processed tobacco. Likewise, transgenic increased-nicotine tobacco would also be more economical than adding synthetic nicotine or nicotine analogs. Labor, time and various other resources would be saved since growing additional tobacco for nicotine extraction, extracting the nicotine, and then adding such nicotine to processed tobacco would not have to be carried out. Once the transgenic plants are produced, they internally produce the additional nicotine required very efficiently and there are no additional incremental costs.

It is currently prohibited to add nicotine and organic acid salts of nicotine (as proposed in U.S. Pat. Nos. 4,830,028, 4,836,224 and 5,031,646) to tobacco products in many countries, including the United States. In many countries, nicotine and organic acid salts of nicotine are not on the list of allowed additives for tobacco products. The term "tobacco product" used herein includes but is not limited to cigarettes, cigars, cigarette tobacco, pipe tobacco, chewing tobacco, snuff, lozenges and any other nicotine delivery device that is not a nicotine replacement product used for nicotine replacement therapy.

Another advantage of the above low TNR cigarette embodiments is that increased-nicotine tobacco is safer than mechanically extracting nicotine from a source, transporting it, and then adding it to tobacco during processing, because nicotine in its pure form is highly toxic. Nicotine is difficult to maintain in pure form since it is easily oxidized. Storage of pure nicotine would add costs and risks.

A potential disadvantage of the above methods may be increased TSNAs produced from the higher levels of alkaloids, which are nitrosamine precursors. This would be offset by the reduction of whole smoke deliveries, within which TSNAs are contained. TSNAs are just one class of multiple carcinogens in tobacco smoke. Appropriate curing methods along with low TNR cigarettes will reduce this potential disadvantage to an acceptable level (Peele, D. M., et al., "Formation of Tobacco Specific Nitrosamines in Flue-Cured Tobacco", CORESTA 1999 AGRO-PHYTO Proceedings, Suzhou, China 1999).

If a low TNR cigarette yields a 35 percent reduction in whole smoke deliveries to smokers (including tar and harmful gases), compared to an average light or ultra-light conventional cigarette, yet its yield of TSNAs is slightly higher, one could hypothesize that epidemiological studies would eventually prove that this embodiment would have significant reduced-risk advantages.

The low TNR cigarette of this embodiment preferably employs tobacco material from a transgenic *Nicotiana tabacum* variety or cultivar that has a phenotype characterized by an increased nicotine level, compared to the variety or cultivar lacking the transgene, as described above, and by a cured, reducing sugar content that is very high, relative to the range of sugar-content values represented by widely commercialized varieties and cultivars. Preferred ranges of tobacco variety reducing sugar contents are from about 11 percent to about 20 percent, or more preferably over 20 percent. Illustrative of such very high sugar content *N. tabacum* varieties are K 394, NC 2326, and GL 939, which have a three-year average, cured, reducing sugar content of 15.7 percent, 15.5 percent, and 15.2 percent, respectively (2000 Official Flue-Cured Variety Test at the University of Georgia, Tifton).

In this regard, the terms "cultivar" and "variety" are used synonymously to refer to a group of plants within the species, *N. tabacum*, that share certain constant characters separating them from the typical form and from other possible varieties within that species. While possessing at least one distinctive trait, a variety also may be characterized by a substantial amount of overall variation between individuals within the variety, based primarily on the Mendelian segregation of traits among the progeny of succeeding generations. A "line," as distinguished from a "variety," denotes a group of plants which display less variation between individuals, generally (although not exclusively) by virtue of several generations of self-pollination. In addition, a "line" is defined, for the purpose of the present invention, sufficiently broadly to include a group of plants vegetatively propagated from a single parent plant, using tissue culture techniques. The use of such lines to develop new hybrids is described in U.S. Pat. Nos. 4,326,358 and 4,381,624.

A "nicotine buffer" helps maintain the pH of cigarette smoke. As nicotine is a major volatile base present in cigarette smoke, smoke pH imparts an important role in sensory perception. Sugar acts as a nicotine buffer, reducing any harshness from the increased nicotine; hence, a high sugar content is beneficial, whether the sugar is natural to the tobacco plant or is added, e.g., as high fructose corn syrup, sucrose, invert sugar, licorice extract, carob bean and extract, and cocoa and cocoa extracts during tobacco processing.

"Reducing sugar(s)" are any sugar (monosaccharide or polysaccharide) that has a free or potentially free aldehdye or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. Generally, there is an inverse relationship between sugar content and alkaloid content across tobacco varieties, within the same variety, and within the same plant line caused by planting conditions. For example, the lower the nitrogen is in tobacco's soil, the lower the nicotine levels but the higher sugar levels. Increased rain produces lower nicotine levels and higher sugar levels.

Cigarettes with low TNRs may produce a harsh and irritating smoke, especially in regards to throat and nasal irritation. A source of this harshness is generally ascribed to the amount of "free" or "volatile," unprotonated nicotine in the smoke. In general, at a smoke pH of 5.4, nicotine is 100% protonated. As smoke pH increases above 5.4, the more "free" nicotine is present in the smoke, which is a cause of harshness. The pH of cigarette smoke is predominantly determined by the sugar and alkaloid content of tobacco filler. Sugar combustion produces acidic by-products which lowers the pH and helps to reduce harshness. For example, cigarettes containing all flue-cured tobacco (which generally contain a higher sugar content than if they contained both flue-cured and burley tobacco) have a smoke pH of about 5.0 to about 6.0 which is calculated to produce 0-1% unprotonated nicotine.

Higher nicotine tobaccos, such as burley, (which generally contain a lower sugar content than flue-cured) will generally produce a smoke that has a higher smoke pH. American-blended cigarettes (flue-cured tobacco blended with burley and possibly oriental) have a smoke pH of about 5.5 to about 6.5 which is calculated to produce 0.3-3% unprotonated nicotine (Morie, G. P., (1972), Fraction of protonated and unprotonated nicotine in tobacco smoke at various pH values, Tob. Sci., 16, 167.) Thus, cigarettes produced from transgenic high-nicotine tobacco with a TNR of below about 9 will usually have a pH greater than 6.5 and might be considered harsh to smokers-unless enough sugar or other nicotine buffer(s) are present in the filler. By using very high sugar tobacco or adding enough sugar to the filler, the pH will be reduced and the low TNR cigarette will have an acceptable taste. This pH reduction can also be accomplished by increasing the fatty acid content in the filler, as described below.

Another embodiment of the present invention provides a method of making a cigarette comprising providing an increased-alkaloid transgenic plant or plant portion, as compared to a non-transformed control plant or plant portion, of a species of the genus *Nicotiana*, crossing the plant with a plant of the species *Nicotiana tabacum* to obtain a progeny plant, and producing a cigarette comprising the progeny plant, with the cigarette having a tar-to-nicotine yield ratio of between about 3 and about 8, as measured by the FTC or ISO method. The advantages of this new plant are that various increased alkaloids other than nicotine (including unique nicotine to total alkaloid ratios) of various *Nicotiana* species are combined with the desired traits of *Nicotiana tabacum*. For example, the primary alkaloid in *Nicotiana glauca* is anabasine. U.S. Pat. No. 6,534,527 describes *N. glauca* as useful in relieving nicotine cravings.

Another embodiment of the present invention provides a method of making a cigarette comprising providing a reduced-nicotine transgenic *Nicotiana tabacum* plant or plant portion having a reduced nicotine content as compared to a non-transformed control plant or plant portion, crossing the reduced-nicotine plant with a *Nicotiana rustica* plant to obtain a progeny plant, and producing a cigarette comprising the progeny plant, with the progeny plant or plant portion exhibiting increased nicotine as compared to the *Nicotiana tabacum* plant from which the transgenic plant or plant portion was produced. The progeny plant is then used to produce a cigarette having a tar-to-nicotine yield ratio of between about 3 and about 8, as measured by the FTC or ISO method. The advantages of this new plant are again that unique nicotine to total alkaloid ratios can be obtained.

Pursuant to conventional breeding techniques, as described by Wemsman, et al., in 2 PRINCIPLES OF CULTIVAR DEVELOPMENT: CROP SPECIES (Macmillan 1997), a stable transformant, regenerated from tobacco material that contains a suitable transgene, is employed to introgress a high-nicotine trait into a commercially acceptable genetic background, thereby obtaining a tobacco cultivar or variety that combines a high nicotine level with very high sugar content in the range, for example of about 14 percent to about 20 percent, more preferably 20 percent to 30 percent, and more preferably yet over 30 percent. While any high sugar tobacco background may be used, for purposes of this embodiment, the cultivar or variety thus obtained is preferably of the flue-cured type. Following successive rounds of crossing and selection, progeny are selected having both high nicotine and high sugar content.

Because tobacco is amenable to genetic studies, any transgene can be introduced into a suitable tobacco background using techniques and methods well known in plant molecular biology. As described by Miki et al. in METHODS IN PLANT MOLECULAR BIOLOGY AND BIOTECHNOLOGY (CRC Press 1993), any of transfection, infection, transformation, natural uptake, electroporation, and biolistics can be used for introducing a transgene into any genetic background. For example, and in accordance with the present embodiment, a gene conferring a high sugar phenotype is introduced into a host tobacco plant cell, thereby generating a plant expressing elevated sugar content. For instance, a tobacco cell is transformed with a gene encoding an enzyme or transcription factor that up-regulates sugar synthesis, such as a gene conferring elevated levels of glucose and fructose. Following successive selection, progeny plants having elevated sugar content are selected.

Illustrative of the present invention, a transgene conferring a high-nicotine phenotype can be introduced into a high-sugar tobacco background. Any gene or portion of a gene that encodes a product conferring increased nicotine biosynthesis may be employed for transformation. Illustrative in this regard are genes encoding arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), respectively. Once a transgene that confers a high-nicotine phenotype is introduced into a high-sugar tobacco plant, successive rounds of selection are exploited, in a conventional manner, for identifying and selecting a tobacco line that co-segregates for both high nicotine and high sugar content. Nicotine and sugar content are analyzed by standard methods.

In another embodiment, a gene conferring a high-nicotine phenotype is introduced into a plant expressing elevated fatty acid synthesis. Using well-known plant molecular biology techniques, any gene or portion of a gene that confers increased fatty acid synthesis is employed for transformation. Illustrative in this regard are genes encoding and/or regulating the synthesis of saturated fatty acids, such as the genes encoding stearic acid and palmitic acid. Progeny plants are assayed for elevated fatty acid synthesis using methods well-known in the art, such as PCR, northern analysis, and chromatographic analyses. Following the identification and selection of a stable line having elevated fatty acid synthesis, a transgene conferring a high-nicotine phenotype is introduced into the elevated fatty acid synthesis line. Successive rounds of selection are exploited, in a conventional manner, for identifying and selecting a tobacco line that co-segregates for both high nicotine and elevated fatty acid content. Nicotine and fatty acid levels are analyzed by standard methods.

A variety or cultivar is considered "true-breeding" for a particular trait if it is genetically homozygous for that trait to the extent that, when the variety or cultivar is self-pollinated, a significant amount of independent segregation of the trait among the progeny is not observed. In gauging the true-breeding character of material in this context, those skilled in tobacco breeding will recognize that the sugar level of tobacco leaf varies among plants of an identical line, because different crops are not exposed to identical levels of sunlight. Sugar-level variability exists even within a single plant. Thus, lower leaves usually are shaded by the upper leaves, while plants on the edges of a row tend to receive more sunlight than plants in the center of a row. For these reasons, sugar level generally increases with stalk position going up the plant from bottom to top. Through normal experimentation, the skilled breeder would take these and other considerations into account when developing a cultivar or variety that, in accordance with one embodiment of the present invention, is true-breeding for high nicotine levels and very high sugar content.

In another embodiment, any potential harshness from the increased nicotine in the smoke produced from the subject invention is reduced through the addition of the appropriate amounts of reducing sugars to the tobacco filler. Typically these reducing sugars are added to the tobacco casing in the form of high fructose corn syrup, honey or licorice. Optimum results are typically obtained for sugar to nicotine ratios of around 3.3 parts sugar to 1 part nicotine of the tobacco filler on a dry weight basis (Status update of sugar/nicotine balance technology assessment (1992) RJ Reynolds documents, Bates 512842551/2).

However, this ratio could be adjusted according to smoker taste preferences so that the sugar/nicotine ratio range is between about 3 and about 5. As previously discussed, the pH of the smoke of low TNR cigarettes and the reducing sugar content of its filler must be considered when adjusting sugar additives. For this analysis, the nicotine content in tobacco is determined by extraction and analysis by Gas Chromatography. Natural tobacco sugar levels are determined by extraction and analysis by High Performance Liquid Chromatography. Having obtained the amounts of natural nicotine and sugars on a dry weight basis, the amount of additional sugars is determined to obtain the desired ratio.

In another embodiment, fatty acids may be used as nicotine buffers. For example, myristic and palmitic acids may be added to tobacco fillers to function as nicotine buffers. Also, fatty acids, such as found in high butterfat cocoa or coconut oil, may be added to the tobacco casing. Alternatively, a tobacco plant may be genetically modified to produce elevated fatty acids in tobacco leaf tissues.

It will be appreciated that tobacco plants of the present invention may not be "transgenic," i.e. may not contain nucleic acid sequences from other organisms incorporated in their genome, yet the levels of nicotine, sugars or fatty acids be modified by producing plants or plant cells through targeted mutagenesis of specific nucleic acid sequences by introduction of nucleic acids that induce DNA repair or recombination (Beetham et al., 1999; Zhu et al., 2002; WO 03/013226), or introduction of modified viruses which may produce similar end results as "increased-nicotine transgenic plants," "reduced-nicotine transgenic plants," "increased-sugar transgenic plants," and increased-fatty acid transgenic plants described herein. A "Precise Breeding" method (U.S. Pub. No. 20040107455), in which only nucleic acid sequences derived from the target species or sexually compatible species are introduced into the genome of the target plant, may be used to produce plants that are "increased-nicotine plants," "reduced-nicotine plants," "increased-sugar plants," and increased-fatty acid plants described herein.

2. Low TNR Cigarettes (by Adding Nicotine from Transgenic Increased-Nicotine Plants)

A second aspect of the present invention is a method of adding nicotine or a nicotine-containing fraction extracted from an increased-nicotine transgenic plant, as described above, to conventional tobacco or reduced-nicotine tobacco at the required levels.

U.S. Pat. Nos. 4,830,028; 4,836,224 and 5,031,646, describe modification of cigarette filler by addition of organic acid salts of nicotine. In particular, they address addition of nicotine in this manner in order to decrease the tar-to-nicotine yield ratio. A review by the Brown and Williamson Tobacco Company in the Journal of the American Medical Association (volume 274, No. 3, p. 228, 1995) describes Project Ariel covered by U.S. Pat. Nos. 3,258,015 and 3,356,094 (Battelle). These patents describe an aerosol with nicotine added in such a manner capable of reducing the tar-to-nicotine yield ratio of the inventive cigarettes to one quarter of that of conventional cigarettes.

Nicotine-containing fractions, nicotine, or nicotine salts of organic acids obtained from increased-nicotine transgenic plants are added to conventional tobacco or reduced-nicotine transgenic plants by spraying or using any other method to one skilled in the art of tobacco processing and additive applications, with or without propylene glycol or any other solvent, or water, for dissolution, onto whole leaf or cut-rag tobacco. The amount of nicotine that has to be added in designing a low TNR cigarette is a function of the following: (1) the nicotine content and type of tobacco blend being used—American blend cut rag tobacco generally contains approximately 2 to 2.5 percent nicotine, (2) the specifications of the cigarette rod, with consideration of ventilation or porosity properties, (3) the desired TNR of the cigarette, and (4) the specific tar yield desired.

For example, let's assume a cigarette manufacturer wants to create a low TNR cigarette that yields 8 mg tar and the same 1.2 mg nicotine that its full flavor brand style yields as per the FTC/ISO Method. It's full flavor brand style yields 16 mg tar so the goal is for the novel brand style's TNR to be half that of the full-flavor brand style. It is also desired to use the same filler and then add nicotine to create the low TNR cigarette.

The amount of nicotine that the manufacturer would initially add during product development for yields 8 mg tar and of 1.2 mg nicotine is about twice as much as the nicotine content of its filler for its full flavor brand. It will be appreciated by one skilled in the art that the extra ventilation of the light rod will reduce the tar yield at a slightly higher rate than the nicotine yield so that doubling the nicotine of the filler may be slightly too much. However, some nicotine may be lost during the tobacco processing and cigarette manufacturing processes, so doubling the nicotine could be justified. The impact from the duration of such tobacco is stored after the addition of nicotine, but before cigarette manufacturing, must also be evaluated. Since the scale and manner of these processes are different for every manufacturer, it will be appreciated that some trial and error may be necessary.

A light rod that usually yields 8 mg of tar per cigarette can initially be chosen by the manufacturer. The result that is desired is a cigarette that yields 8 mg tar and 1.2 mg nicotine, thereby cutting tar more than half yet keeping nicotine yield the same as most full-flavor cigarettes.

A selected amount of tobacco, after adding nicotine, or nicotine salts of organic acids, at about 13 percent moisture is placed into the hopper of a cigarette-making machine. The cigarette-making machine then passes the rolled cigarettes to another machine that puts the filter on the unfiltered rolled cigarette. This step is skipped if non-filter cigarettes are being produced.

The finished cigarettes is then tested using the FTC/ISO Method so that end results can be evaluated. If the cigarette yields 8 mg tar and 1.2 mg nicotine, (a TNR of 6.66) and all of the above considerations have been accounted for, then the development has been completed. If the cigarette is being rated harsh in focus groups due to the extra nicotine, then additives should be added to the filler to help alleviate the problem.

Minor adjustments can be made if the cigarettes manufactured yield more or less than the desired yields. These include changing one of the components of the cigarette rod. Some of the components rods may be modified by varying the types of filters, cigarette paper, plug wraps, the tipping paper (that holds the cigarette rod to the filter), the ventilation holes, and their corresponding variations in combination. For example, if the cigarette is yielding 9 mg of tar and 1.3 mg nicotine, the filtration and/or dilution is slightly increased to reduce both tar and nicotine yields in a very similar proportion. This is usually achieved by specifying the size and quantity of the ventilation holes and the porosity of the filter plug wrap to achieve the desired yield. If the tar yield is on target but the nicotine yield is higher or lower than desired, then the levels of added nicotine can be adjusted accordingly.

Most brands of cigarettes have from about 10 percent of reconstituted tobacco in premium brands to about 30% in discount brands in the filler of the cigarette even though it is not a necessary part of the filler. Another embodiment of the present invention is to add nicotine to the reconstituted portion of the cigarette filler in order to give the cigarettes a lower TNR. Adjustments in the amount of nicotine to add to low TNR cigarettes is another variable which can be accomplished by the manufacturer. Therefore, the nicotine content of the filler is a function of the nicotine content of the tobacco plus the nicotine content of any reconstituted tobacco in the filler, including increased-nicotine recon and/or reduced-nicotine recon, or both. Any combination of the three can be utilized.

A 1975 paper from the Philip Morris Document Website (Bates 2056140416, Titled "Low Delivery Cigarettes and Increased Nicotine/Tar Ratios, A Replication") describes results from a taste panel of cigarettes with increased nicotine/tar ratios. It was found that a cigarette with a 10 mg tar delivery and a nicotine/tar ratio of 0.09 (TNR equivalent of 11) was equal in acceptability and strength to the Marlboro® full-flavor control (at such time-18 mg tar, 1.03 mg nicotine, nicotine/tar ratio of 0.06), which equates to a TNR of 16.66.

It will be appreciated by one skilled in the art that extracting nicotine from increased-nicotine recombinant tobacco for the above embodiments will be more economical and efficient than doing so from conventional tobacco since less plants will have to be grown and processed to obtain a sufficient amount of nicotine.

3. Reduction of Harmful Tobacco-Specific Nitrosamines in Tobacco Products

It is well known in the tobacco industry that tobacco-specific nitrosamines (TSNAs), commonly referred to as a carcinogen in tobacco, form predominantly while tobacco is curing. While other TSNAs are present in tobacco, the four that are generally agreed to be the most harmful are the following: N'-nitrosonornicotine (NNN), 4-(N-nitrosomethylamino)-1-(3-pyridyl)-1-butan-one (NNK), N'-nitrosoanatabine (NAT), N'-nitrosoanabasine (NAB). TSNAs in curing tobacco are formed from the minor alkaloid precursors (Wiernik, et al., 1995, "Effect of air-curing on the chemical composition of tobacco", *Recent Advances in Tobacco Science*, 21, 39-80). As used herein, tobacco-specific nitrosamines or TSNAs are selected from of the group of the following: NNN, NNK, NAT, and NAB.

TSNAs are predominantly analyzed by Gas Chromatography with Chemiluminescence Detection following solvent extraction (Charles Risner, et al., Quantification of Tobacco Specific Nitrosamines in Tobacco, Tobacco Science, 38 (1-6), 1994.). An alternate method for separation and analysis utilizes supercritical fluid extraction with Gas Chromatography/Mass Spectrometric Detection (Siqing Song, et al., Supercritical fluid extraction and GC/MS for the analysis of tobacco-specific nitrosamines in cigarettes, Analytical Chemistry, 1999, 71, 1303-1308). More recently, a rapid procedure using ammonium acetate extraction followed by Liquid Chromatography using Mass Spectrometry (MS/MS) has been proposed (Karl Wagner, et al., The rapid and quantitative analysis of tobacco specific nitrosamines in whole tobacco and mainstream smoke using LC/MS/MS with positive ion electrospray, 55th Tobacco Science Research Conference 2001).

The level of nitrosamines is generally positively correlated to nicotine content since alkaloids are usually present in proportion to nicotine content. Generally, for most varieties of *Nicotiana tabacum*, nicotine makes up about 90 percent of the plant's total alkaloid content. Therefore, another embodiment of the present invention is to use reduced-nicotine transgenic tobacco and add extracted nicotine, nicotine salts derived from organic acids (derived from conventional or genetically modified increased-nicotine tobacco), or synthesized nicotine, in free base or combined with organic acids, to in order to create a cigarette or other tobacco products with virtually no nitrosamines or minor alkaloids, yet one that yields a conventional amount of nicotine. This method is utilized with genetically modified reduced-nicotine tobacco by adding only enough nicotine to provide the same yield as conventional cigarettes with the FTC/ISO Method, e.g., from 0.05 to 1.5 mg per cigarette.

Genetically altering the alkaloid content in tobacco has been carried out by altering quinolate phosphoribosyl transferase (QPT) and putrescine methyltransferase (PMT). FIG. 4 shows how alkaloids including Nor-Nicotine have been reduced by reducing QPRTase in a burley variety to create a low alkaloid transgenic variety named Vector 21-41. This tobacco variety contains very low levels of TSNAs. The Vector 21-41 variety is protected by the Plant Variety Protection Office and its Plant Variety Protection Number is 200100039.

"Transformed root lines were produced that contained markedly reduced PMT activity, with a concomitant reduction in nicotine content compared to controls" (Yupynn Chintapakorn and John D. Hamill, Plant Molecular Biology 53: 87-105, 2003. © 2003 Kluwer Academic Publishers. 87). One of the minor alkaloids, nornicotine, is negatively correlated with tobacco quality and cigarette taste (Natural Tobacco Flavor", Roberts, D. L., *Recent Advances in Tobacco Science,* 14, pg. 49-81, 1988). A cigarette product produced with nicotine as the only alkaloid should be highly acceptable on this basis alone.

Reduced-nicotine tobacco plants used to carry out the present invention are, in general, recombinant tobacco plants that contains and express a heterologous nucleotide, the expression of which heterologous nucleotide down-regulates an enzyme such as quinolate phosphoribosyl transferase (QPRTase), putrescine methyltransferase (PMTase), arginine decarboxylase, ornithine decarboxylase, S-adenosylmethionine synthetase, NADH dehydrogenase, or phosphoribosylanthranilate isomerase (PRAD in the plant, and thereby reduces the production of nicotine in the plant. Suitable recombinant plants are disclosed in M. Conkling et al., PCT Application WO98/56923 (published Dec. 17, 1998) and in M. Timko, PCT Application WO0/67558 (published Nov. 16, 2000). In general, the heterologous nucleotide comprises at least a segment of a nucleic acid encoding the enzyme to be down-regulated, in sense or antisense orientation.

Preferably the reduced-nicotine tobacco also contains reduced (e.g., by at least 90, 95 or 99 percent by weight or more) levels of tobacco-specific nitrosamines as compared to that which would be found in the plant in the absence of corresponding reductions in nicotine.

Another embodiment of the present invention utilizes a reduced-nicotine recombinant plant that has reduced quinolate phosphoribosyl transferase (QPRTase) expression relative to a non-transformed control plant, such recombinant plant comprising recombinant plant cells containing: an exogenous DNA construct comprising, in the 5' to 3' direction, a promoter operable in such plant cell and a heterologous DNA encoding at least a segment of a plant quinolate phosphoribosyl transferase mRNA, such heterologous DNA operably associated with such promoter, and with such heterologous DNA in sense or antisense orientation; such plant exhibiting reduced QPRTase expression compared to a non-transformed control plant and reduced-nicotine content as compared to a non-transformed control plant.

Another embodiment of the present invention may be carried out with a reduced-nicotine recombinant plant that has reduced putrescine N-methyltransferase (PMTase) expression relative to a non-transformed control plant, such recombinant plant comprising recombinant plant cells containing: an exogenous DNA construct comprising, in the 5' to 3' direction, a promoter operable in such plant cell and a heterologous DNA encoding at least a segment of a plant PMT mRNA, such heterologous DNA operably associated with such promoter, and with such heterologous DNA in sense or antisense orientation; such plant exhibiting reduced PMT expression compared to a non-transformed control plant and reduced-nicotine content as compared to a non-transformed control plant. Still other embodiments may be carried out in like manner with the other enzymes listed above.

Nucleic acid constructs as described above may include insulator elements upstream (5' to) and/or downstream (3' to) of the construct described above, as set forth (for example) in U.S. Pat. Nos. 6,100,448 and 6,037,525 to Thompson et al. In addition, constructs as described above may include matrix (or scaffold) attachment regions upstream and/or downstream of the construct described above, as set forth (for example) in U.S. Pat. Nos. 5,773,695 and 5,773,689 to Thompson et al.

In another embodiment of the present invention, plants utilized may contain a plurality of recombinant nucleic acids that down-regulate a plurality of enzymes in the nicotine synthesis pathway. The benefits of utilizing more than one recombinant nucleic acid is that nicotine levels can be decreased to a greater extent (versus if one such nucleic acid is utilized), possibly to zero, and different desired alkaloid ratios (e.g., the ratio of nicotine to total alkaloids) may be accommodated, if preferred.

Thus, another embodiment of the present invention utilizes a reduced-nicotine recombinant plant that has both reduced QPRTase and reduced PMTase expression relative to a non-transformed control plant, such recombinant plant comprising recombinant plant cells containing: (i) a first exogenous DNA construct comprising, in the 5' to 3' direction, a promoter operable in such plant cell and a heterologous DNA encoding at least a segment of a plant quinolate phosphoribosyl transferase mRNA, such heterologous DNA operably associated with such promoter; and (ii) a second exogenous DNA construct comprising, in the 5' to 3' direction, a promoter operable in such plant cell and a heterologous DNA encoding at least a segment of a plant PMT mRNA, such heterologous DNA operably associated with such promoter, and with such heterologous DNA in sense or antisense orientation; such plant exhibiting reduced PMT expression compared to a non-transformed control plant and reduced-nicotine content as compared to a non-transformed control plant. It will be appreciated that, where sense and antisense down-regulation are described herein, other techniques such as the use of inverted repeats that produce dsRNA that induces gene silencing, ribozymes, or interfering complementary mRNA may be used. It will also be appreciated that a single DNA construct may be used that reduces the activity of more than one enzyme. For example, one DNA construct may be used to reduce both QPRTase and PMTase.

Examples of nucleic acid sequences that may be used to carry out the present invention include, but are not limited to, known DNA encoding the tobacco quinolate phosphoribosyl transferase gene (NtQPT1); (see, e.g., PCT Application WO98/5556923 to Conkling et al.); DNA encoding tobacco putrescine N-methyltransferase such as PMT1, PMT2, PMT3 and PMT4; DNA encoding tobacco arginine decarboxylase such as ADC1 and ADC2; DNA encoding tobacco ornithine decarboxylase (ODC); DNA encoding tobacco S-adenosylmethionine synthetase (SAMS); DNA encoding tobacco NADH dehydrogenase, and DNA encoding tobacco phosphoribosylanthranilate isomerase (PRAI) (which are known and described in PCT Application WO 00/67558 to M. Timko et al.).

Conditions which permit other DNA sequences which code for expression of a protein having a desired enzyme activity as described above to hybridize to DNA as described above, or to other DNA sequences encoding the enzyme protein as given above, can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60.degree. C. or even 70.degree. C. to DNA encoding the protein given above in a standard in situ hybridization assay. See J. Sambrook et al., Molecular Cloning, A Laboratory Manual (2d Ed. 1989, Cold Spring Harbor Laboratory). In general, such sequences will be at least 65% similar, 75% similar, 80% similar, 85% similar, 90% similar, or even 95% similar, or more, with the sequence given above, or DNA sequences encoding proteins given above. (Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.)

The heterologous sequence utilized in the methods of the present invention may be selected so as to produce an RNA product complementary to the entire message encoding the enzyme sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA. Suitable antisense sequences may be from at least about 12, 14 or 15 to about 15, 25, or 35 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof (e.g., by the addition of 1 to 4 or 8 additional nucleic acid residues). The antisense product may be complementary to coding or non-coding (or both) portions of naturally occurring target RNA. The particular anti-sense sequence and the length of the anti-sense sequence will vary depending upon the degree of inhibition desired, the stability of the anti-sense sequence, and the like. One of skill in the art will be guided in the selection of appropriate enzyme antisense sequences using techniques available in the art and the information provided herein.

As indicated above, the present invention may also be carried out with plants that implement sense co-suppression of nicotine production. Sense DNAs employed in carrying out the present invention are of a length sufficient to, when expressed in a plant cell, suppress the native expression of the plant enzyme as described herein in that plant cell. Such sense DNAs may be essentially an entire genomic or complementary DNA encoding the enzyme, or a fragment thereof with such fragments typically being at least 15 nucleotides in length. Methods of ascertaining the length of sense DNA that results in suppression of the expression of a native gene in a cell are available to those skilled in the art. The present invention may also be carried out with plants that contain DNAs encoding double stranded RNAs comprising complementary antisense and sense sequences that when expressed are capable of suppressing or silencing endogenous genes containing the sequences. Suitable complementary regions may be from at least about 20 to 25 nucleotides and may be separated by at least about 5 nucleotides.

In still another embodiment of the present invention, *Nicotiana* plant cells are transformed with a DNA construct containing a DNA segment encoding an enzymatic RNA molecule (e.g., a "ribozyme"), which enzymatic RNA molecule is directed against (e.g., cleaves) the mRNA transcript of DNA encoding a plant enzyme as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif. Ribozyme cleavage sites within an RNA target may initially be identified by scanning the target molecule for ribozyme cleavage sites (e.g., GUA, GUU or GUC sequences). Once identified, short RNA sequences of 15, 20, 30 or more ribonucleotides corresponding to the region of the target gene containing the cleavage site may be evaluated for predicted structural features. The suitability of candidate targets may also be evaluated by testing their accessibility to hybridization with complimentary oligonucleotides, using ribonuclease protection assays as are known in the art. DNA encoding enzymatic RNA molecules may be produced in accordance with known techniques. See, e.g., T. Cech et al., U.S. Pat. No. 4,987,071; Donson et al., U.S. Pat. No. 5,589,367; Torrence et al., U.S. Pat. No. 5,583,032; Joyce, U.S. Pat. No. 5,580,967; Wagner et al., U.S. Pat. No. 5,591,601; and U.S. Pat. No. 5,622,854. Production of such an enzymatic RNA molecule in a plant cell and disruption of enzyme protein production reduces enzyme activity in plant cells in essentially the same manner as production of an antisense RNA molecule: that is, by disrupting translation of mRNA in the cell which produces the enzyme. The term 'ribozyme' is used herein to describe an RNA-containing nucleic acid that functions as an enzyme (such as an endoribonuclease), and may be used interchangeably with 'enzymatic RNA molecule'.

In still another embodiment of the invention, down-regulation of nicotine production may be achieved by employing translational Inhibition of mRNA utilizing interfering complementary mRNA, as set forth in U.S. Pat. No. 5,272,065.

To produce a tobacco plant having decreased enzyme levels, and thus lower nicotine content, than an untransformed control tobacco plant, a tobacco cell may be transformed with an exogenous transcriptional unit comprising a partial enzyme nucleic acid sequence, a full-length enzyme nucleic acid sequence, in the sense or antisense orientation with appropriate operably linked regulatory sequences or a sequence encoding a ribozyme as described above. Appropriate regulatory sequences include a transcription initiation sequence ("promoter") operable in the plant being transformed, and a polyadenylation/transcription termination sequence. Standard techniques, such as restriction mapping, Southern blot hybridization, and nucleotide sequence analysis, are then employed to identify clones bearing enzyme sequences in the antisense orientation, operably linked to the regulatory sequences. Tobacco plants are then regenerated from successfully transformed cells. It is most preferred that the antisense sequence utilized be complementary to the endogenous sequence, however, minor variations in the exogenous and endogenous sequences may be tolerated. It is preferred that the antisense DNA sequence be of sufficient sequence similarity that it is capable of binding to the endogenous sequence in the cell to be regulated, under stringent conditions as described below. Particular techniques for producing recombinant tobacco plants are known to those skilled in the art and are explained in greater length in M. Conkling et al., PCT Application WO98/56923 (published Dec. 17, 1998) and in M. Timko, PCT Application WO00/67558 (published Nov. 16, 2000), noted above.

The reduced-nicotine tobacco variety, Vector Burley 21-41, was developed by genetically modifying Burley 21 LA as described in U.S. Pat. No. 6,586,661. Burley 21 LA is a variety of Burley 21 with substantially reduced levels of nicotine as compared with Burley 21 (e.g., Burley 21 LA has 8% the nicotine levels of Burley 21, see Legg et al., (1971) Can. J. Genet. Cytol. 13:287-91; Legg et al., (1969) J. Hered. 60:213-17). Vector Burley 21-41 is most similar to the parent variety, Burley 21 LA. In general, Vector Burley 21-41 is similar to Burley 21 LA in all assessed characteristics, with the exception of alkaloid content (e.g., nicotine and nornicotine). Vector Burley 21-41 may be distinguished from the parent Burley 21 LA by its substantially reduced content of nicotine, nornicotine and total alkaloids.

As shown in FIG. 4, total alkaloid concentrations in Vector 21-41 are reduced to approximately 10 percent of the levels in the parent Burley 21 LA. Nicotine and nor-nicotine concentrations are less than approximately 6.7% and 32%, respectively in Vector Burley 21-41 as compared with Burley 21 LA. QPRTase levels are positively correlated to nicotine and other tobacco alkaloids including anabasine and anatabine, which in turn produce NAB and NAT. See FIG. 5.

In still another embodiment of the present invention to add an equal amount of nicotine, or nicotine salts of organic acids, and nicotine analogs (compared to conventional tobacco) to reduced-nicotine tobacco to create tobacco products with reduced TNSAs. Conventional methods to one skilled in the art of tobacco processing, including the use of tobacco additives and flavorings, are used to add nicotine to such tobacco products.

Another embodiment of the present invention is to add an even greater amount of nicotine to reduced-nicotine tobacco (compared to conventional tobacco) to create a low TNR cigarette. The major advantage of this method is that virtually no nitrosamines form on the tobacco when the tobacco is curing due to the absence of nicotine, or minor alkaloids. Cigarettes produced by this method not only have the advantages of low TNR cigarettes, but also contain virtually no nitrosamines or minor alkaloids if QPRT is reduced or eliminated. Another embodiment of the present invention is to utilize reduced-nicotine tobacco and then add nicotine so that a conventional amount of nicotine is present for the following products: cigar filler or wrapper, roll-your-own tobacco for cigarettes, pipe tobacco, chewing tobacco, snuff, reconstituted tobacco, and all other versions of smokeless tobacco. The advantages being that these products are extremely low in TSNAs and/or minor tobacco alkaloids.

4. Production of Improved Expanded or Puffed Tobacco Using Increased-Nicotine Transgenic Tobacco More than 150 patents have been issued related to tobacco expansion (e.g., U.S. Pat. No. 3,991,772). The expansion process gives greater filling power to the tobacco so less tobacco weight in used in the cigarette. An advantage from using expanded tobacco is reduced tar delivery. Expanded tobacco is particularly useful in making low-tar delivery cigarettes. Carlton® cigarettes, which has had claims that it is the lowest tar and nicotine delivery cigarette, is reportedly made with a very large percentage of expanded tobacco. However, use of expanded tobacco also results in reduced nicotine delivery, which may result in compensation.

The main benefit of expanded increased-nicotine transgenic tobacco is that such tobacco provides reduced tar delivery while about maintaining nicotine delivery, resulting in a cigarette with reduced tar delivery and a reduced TNR. For example, a tobacco blend incorporating increased-nicotine from transgenic tobacco may deliver 16 mg tar and 2.0 mg of nicotine. Expanding this tobacco 100% would give tobacco filler, which would be about one-half the weight of the unexpanded tobacco, but it would occupy the same volume in the cigarette. The smoke delivery of this cigarette would be around 8 mg tar and 1.0 mg nicotine with a INR of 8, without filter ventilation.

Any method for expansion of tobacco known in the art may be used in the present invention. The most common method used today incorporates liquid carbon dioxide (U.S. Pat. Nos. 4,340,073 and 4,336,814). Liquid propane has also been used for making commercial cigarettes, predominantly in Europe (U.S. Pat. No. 4,531,529). Liquid propane offers advantages over carbon dioxide since higher degrees of expansion are possible, in the range of 200%. Under pressure, the liquid carbon dioxide (or liquid propane) permeates the tobacco cell structure. When the tobacco is rapidly heated the carbon dioxide (or liquid propane) expands the cell back to its pre-cured size.

It is another embodiment of the present invention to utilize increased-nicotine transgenic tobacco, preferably tobacco that was created from a high-sugar and/or high fatty acid background and create expanded tobacco from such transgenic tobacco to produce a low TNR cigarette.

It is another embodiment to utilize deproteinized tobacco, preferably extracted from reduced-nicotine transgenic tobacco, and create expanded tobacco from such deproteinized tobacco. A cigarette containing deproteinized expanded tobacco and increased-nicotine transgenic tobacco is produced.

5. Production of Reconstituted Tobacco

It is another embodiment of the present invention to produce reduced-exposure tobacco products, which may include low TNR cigarettes, by utilizing the previous inventions in 1-3 above, deproteinized tobacco fiber, and freeze dried tobacco in any combination and in conjunction with reconstituted tobacco.

The process to produce sheets of reconstituted tobacco ("recon") began during the 1950s. U.S. Patent Nos. that describe such processes include: U.S. Pat. Nos. 3,499,454, 4,182,349, 4,962,774, and 6,761,175. Recon is traditionally produced from tobacco stems and/or smaller leaf particles that closely resembles a typical paper making process. The tar and nicotine yields of reconstituted tobacco are lower than those from equivalent quantities of whole tobacco leaf. This process entails processing the various tobacco portions that are to be made into Recon. After the Recon sheets are produced they are cut into a size and shape that resembles cut rag tobacco made from whole leaf tobacco. This cut recon then gets mixed with cut-rag tobacco and is ready for cigarette making.

Cigarettes can be manufactured with all recon, no recon, or any combination thereof. Most major brands have at least 10% of Recon in the Filler.

The main benefit of increased-nicotine transgenic tobacco used for recon is that such tobacco will reduce the tar yield of cigarettes, while about maintaining nicotine yield.

It is another embodiment of the present invention to add nicotine, or nicotine salts, to produce recon, which is made from reduced-nicotine transgenic tobacco or any non-tobacco plant material including but not limited to herbal blends so that when such reconstituted sheet is burned it yields substantially less tobacco-specific nitrosamines and other carcinogens produced from conventional cigarettes, yet satisfactory amounts are nicotine are present.

It is another embodiment of the present invention to utilize increased-nicotine transgenic tobacco, preferably such tobacco that was created from a high-sugar and/or high fatty acid background and create recon from such transgenic tobacco to produce a low TNR cigarette. Another embodiment increases the sugar content, the fatty acid content, or both of the recon during processing.

Recon from Tobacco Fiber

Patents describing processes of removing proteins from tobacco, thereby creating "deproteinized tobacco fiber" are described in U.S. Pat. Nos. 4,289,147 and 4,347,324. Tobacco fiber is a major byproduct after removing protein. The fibrous remains from deproteinized tobacco can be included in any percentage as an ingredient of reconstituted tobacco. Cigarettes made from deproteinized tobacco have a different taste than conventional cigarettes. However, appropriate amounts of additives, including flavorings and nicotine, could be added to help alleviate this taste deficiency.

Cigarettes containing deproteinized tobacco have a significant advantage over conventional cigarettes since they would produce reduced levels of carcinogens and harmful combustion products. "A 71% reduction in protein content of a flue-cured tobacco sheet resulted in an 81% reduction in the TA98 Ames mutagenicity" of the pyrolytic condensate (Clapp, W. L., et al., "Reduction in Ames *Salmonella* mutagenicity of cigarette mainstream smoke condensate by tobacco protein removal", *Mutation Research*, 446, pg 167-174, 1999). Previous research in this area had determined that tobacco leaf protein might be the principal precursor of mutagens in tobacco smoke condensate (Matsumoto, et al., "Mutagenicities of the pyrolysis of peptides and proteins", *Mutation Research*, 56, pg 281-288, 1978).

Extracting tobacco fiber from genetically modified reduced-nicotine tobacco (e.g., Vector 21-41) effectively eliminates virtually all carcinogenic TSNAs such tobacco, since nitrosamines require relatively high concentrations of nicotine and other alkaloids to form at detectable levels. See FIG. 4

Therefore, it is advantageous to utilize reduced-nicotine tobacco in reduced-exposure cigarettes or other tobacco products to further reduce nitrosamines. Nicotine is either left out or introduced later in the process, which can also be in the form of nicotine salts.

Polycyclic aromatic hydrocarbons (PAHs) are formed from high temperature pyrolysis of amino acids, sugars, paraffins, terpenes, phytosterols, celluloses and other components of tobacco. Most of these components are greatly reduced in tobacco fiber, effectively reducing formation of PAHs. Catechols and phenols, recognized carcinogenic co-factors in cigarette smoke, would also be reduced since low levels of soluble sugar are present in tobacco fiber.

Harmful gas phase compounds such as hydrogen cyanide, nitrogen oxides, and carbon monoxide are also reduced when cigarette containing only tobacco fiber is smoked compared to cigarettes made with whole-leaf tobacco. Hydrogen cyanide is formed from burning proteins and chlorophyll. Nitrogen oxides are formed from burning soluble protein, chlorophyll, nitrates, and alkaloids. These components would not be present in significant amounts in deproteinized tobacco. Tobacco fiber has approximately 85 percent less starches and cellulosic material thus reducing the major pyrolytic precursors of carbon monoxide.

It is another embodiment of the present invention to produce reconstituted tobacco that includes extracted tobacco fiber derived from conventional tobacco, reduced-nicotine transgenic tobacco, or increased-nicotine transgenic tobacco.

Recon from Freeze-Dried Tobacco

If the tobacco curing process is circumvented, virtually no TSNAs will be present in traditional tobacco products such as cigarettes, cigar filler or wrapper, roll-your-own tobacco for cigarettes, pipe tobacco, chewing tobacco, snuff, reconstituted tobacco and other preparations made with freeze-dried tobacco would contain virtually no TSNAs since traditional curing processes are eliminated.

Another embodiment of the present invention is the virtual elimination of TSNAs through processing freshly harvested tobacco using lyophilization. This is accomplished by processing freshly harvested tobacco through freeze-drying units located near tobacco farms. Tobacco processed in this manner may be grown in a traditional fashion with spacing of plants or in a biomass setting. In addition to the economic advantages of eliminating the costs associated with the curing process, the tobacco can now be grown in a biomass fashion that can create hundreds of thousands of pounds of fresh tobacco per acre.

By growing tobacco in a biomass setting and immediately freeze drying the fresh tobacco for cigarettes, roll-your-own-tobacco, pipe tobacco, cigar filler or wrapper, chewing tobacco, snuff, and other versions of smokeless tobacco, labor is reduced not only by eliminating the transplant of each plant from greenhouse to the field but also by eliminating traditional harvesting and curing of the tobacco. Also, farmland needed for this purpose is greatly reduced. The yield of tobacco from one acre of tobacco grown in biomass is equivalent to approximately 100 acres of tobacco grown in a traditional manner.

"Tobacco biomass" is achieved by direct sowing an acre of land with copious quantities of tobacco seed within a few inches of each other in the field. Unlike tobacco planted with traditional spacing, individual plants can no longer be differentiated when tobacco is planted in a biomass fashion. An acre of tobacco biomass has the appearance of a continuous, dense, green carpet. U.S. Pub. Pat. App. No. 20020197688 describes such methods.

Lyophilization removes most of the water (~80%) from the weight of fresh harvested tobacco biomass. The result is Freeze Dried Tobacco ("FDT"). FDT is easily pulverized into fine particles suitable for processing into reconstituted tobacco sheet (recon). This recon can be cut and made into any type of tobacco product such as filler for cigarettes, roll-your-own-tobacco, pipe tobacco, cigar filler or wrapper, chewing tobacco, snuff, and other forms of smokeless tobacco. Flavorings and additives, including sugars, can be incorporated into the recon process.

Such recon can be made from 100 percent FDT or in any proportion that consumers prefer. The lyophilization process may have adverse affects on the taste of such tobacco products. Therefore, FDT can even be mixed in any percentage with traditional pulverized, cured tobacco so that the mixture can be made into reconstituted tobacco. Alternatively, FDT can be mixed in any percentages with any forms of traditional tobacco conducive for manufacturing cigarettes, roll-your-own-tobacco, pipe tobacco, and cigar filler or wrapper, chewing tobacco, snuff and other versions of smokeless tobacco in order to satisfy the tastes of the mass market.

Another embodiment of the present invention is to use genetically modified reduced-nicotine tobacco for reducing TSNAs as described above, thereby creating an additional benefit of such cigarettes, roll-your-own-tobacco, pipe tobacco, cigar filler or wrapper, chewing tobacco, snuff and other versions of smokeless tobacco being non-addictive and without any nitrosamines.

It is another embodiment of the present invention to add nicotine, in amounts that deliver the desired physiological response, back to the FDT for uses in cigarettes, cigar filler or wrapper, roll-your-own tobacco for cigarettes, pipe tobacco, chewing tobacco, snuff, and other versions of smokeless tobacco so that they will contain virtually no TSNAs. Cigarettes produced from tobacco fiber obtained from green leaf would have even further reduced TSNAs, since these are overwhelmingly found in cured tobacco.

In another embodiment of the present invention, *Nicotiana rustica* and/or increased-nicotine transgenic *Nicotiana tabacum* are freeze dried after harvest and are incorporated into recon. The benefits are that the high alkaloid content is preserved for low TNR cigarettes and that the tobacco curing step is saved. Also, the associated increase in TSNAs with high alkaloid tobaccos will not materialize.

What is claimed is:

1. A cigarette comprising a portion of an increased-nicotine transgenic *Nicotiana tabacum* plant, wherein said cigarette is characterized by (i) a tar-to-nicotine yield ratio of between about 3 and about 8, as measured by the FTC or ISO method, (ii) a filler that is not all reconstituted tobacco, and (iii) cigarette smoke having a pH of about 6.5 or lower.

2. A cigarette according to claim 1, wherein said plant expresses at least one heterologous nucleic acid that up-regulates the production of nicotine in said transgenic plant or plant portion.

3. A cigarette according to claim 2, wherein said plant expresses a heterologous nucleic acid encoding at least a segment of QPT and PMT.

* * * * *